US008475735B2

(12) United States Patent
Babu et al.

(10) Patent No.: US 8,475,735 B2
(45) Date of Patent: Jul. 2, 2013

(54) DISPOSABLE IMMUNODIAGNOSTIC TEST SYSTEM

(76) Inventors: Uma Mahesh Babu, Fort Collins, CO (US); Ian Robertson Marshall, Mississauga (CA); Janet Eland-Greenhalgh, Burlington (CA)

( * ) Notice: Subject to any disclaimer, the term of this patent is extended or adjusted under 35 U.S.C. 154(b) by 443 days.

(21) Appl. No.: 11/743,058

(22) Filed: May 1, 2007

(65) Prior Publication Data

US 2007/0202542 A1    Aug. 30, 2007

Related U.S. Application Data

(63) Continuation-in-part of application No. PCT/CA2005/001677, filed on Nov. 1, 2005.

(60) Provisional application No. 60/623,224, filed on Nov. 1, 2004, provisional application No. 60/827,993, filed on Oct. 3, 2006.

(51) Int. Cl.
     *G01N 33/94*         (2006.01)

(52) U.S. Cl.
     USPC .......... 422/420; 422/401; 422/425; 422/430

(58) Field of Classification Search
     None
     See application file for complete search history.

(56) References Cited

U.S. PATENT DOCUMENTS

| | | | |
|---|---|---|---|
| 4,020,046 A | 4/1977 | King et al. | |
| 4,246,339 A | 1/1981 | Cole et al. | |
| 4,578,134 A | 3/1986 | Hartmann | |
| 4,933,092 A | 6/1990 | Aunet et al. | |
| 5,075,078 A | 12/1991 | Osikowicz et al. | |
| 5,096,837 A | 3/1992 | Fan et al. | |
| 5,185,127 A * | 2/1993 | Vonk | 422/408 |
| 5,200,321 A | 4/1993 | Kidwell | |
| 5,229,073 A | 7/1993 | Luo et al. | |
| 5,231,035 A | 7/1993 | Akers, Jr. | |

(Continued)

FOREIGN PATENT DOCUMENTS

| | | |
|---|---|---|
| EP | 0 295 069 | 8/1992 |
| EP | 1328811 B1 | 8/2005 |

(Continued)

OTHER PUBLICATIONS

Donald G. McNeil Jr., Rare Infection Threatens to Spread in Blood Supply, Science Desk, Nov. 18, 2003, Corrections: Dec. 2, 2003.

(Continued)

*Primary Examiner* — Sally Merkling
(74) *Attorney, Agent, or Firm* — Patrick J. Hofbauer

(57) ABSTRACT

A disposable immunodiagnostic test system tests for marker proteins in a sample and includes intimately contacting passage, protein, and absorbent layers. The passage layer is non-porous and has an aperture therethrough. The protein layer is porous, has combinable proteins immobilized thereon, and enables passage of the sample therethrough. The protein layer has an active surface aligned with the passage layer aperture. The sample is introduced onto the protein layer through the passage layer aperture. In positive results, the marker proteins are bound to the combinable proteins and immobilized relative to the protein layer. In negative results, the sample passes through the protein layer, and is absorbed by the absorbent layer. A housing may also be provided, as may a wash structure. The system may be constructed of combustible materials that produce non-toxic by-products upon incineration, preferably enabling ecologically responsible disposal after diagnostic use of the system.

59 Claims, 27 Drawing Sheets

U.S. PATENT DOCUMENTS

| | | | |
|---|---|---|---|
| 5,232,663 A | | 8/1993 | Wilk et al. |
| 5,250,443 A | | 10/1993 | Lindholm et al. |
| 5,275,785 A | | 1/1994 | May et al. |
| 5,354,692 A | | 10/1994 | Yang et al. |
| 5,447,837 A | | 9/1995 | Umovitz |
| 5,452,716 A | | 9/1995 | Clift |
| 5,504,013 A | | 4/1996 | Senior |
| 5,540,962 A | * | 7/1996 | Suskind ............ 428/34.2 |
| 5,552,276 A | | 9/1996 | Mochida et al. |
| 5,602,040 A | | 2/1997 | May et al. |
| 5,622,871 A | | 4/1997 | May et al. |
| 5,656,503 A | | 8/1997 | May et al. |
| 5,712,170 A | | 1/1998 | Kouvonen et al. |
| 5,738,110 A | | 4/1998 | Beal et al. |
| 5,753,517 A | * | 5/1998 | Brooks et al. ............ 436/514 |
| 5,827,749 A | | 10/1998 | Akers, Jr. |
| 6,214,629 B1 | | 4/2001 | Freitag et al. |
| 6,224,831 B1 | | 5/2001 | Stafford et al. |
| 6,290,969 B1 | | 9/2001 | Reed et al. |
| 6,338,852 B1 | | 1/2002 | Reed et al. |
| 6,350,456 B1 | | 2/2002 | Reed et al. |
| 6,379,902 B1 | | 4/2002 | Laqueyrerie et al. |
| 6,458,366 B1 | | 10/2002 | Reed et al. |
| 6,544,522 B1 | | 4/2003 | Skeiky et al. |
| 6,555,653 B2 | | 4/2003 | Alderson et al. |
| 6,592,877 B1 | | 7/2003 | Reed et al. |
| 6,605,475 B1 | | 8/2003 | Taylor et al. |
| 6,605,476 B2 | | 8/2003 | Kobayashi |
| 6,613,881 B1 | | 9/2003 | Alderson et al. |
| 6,617,116 B2 | * | 9/2003 | Guan et al. ............ 435/7.1 |
| 6,627,198 B2 | | 9/2003 | Reed et al. |
| 6,645,733 B1 | | 11/2003 | Daksis et al. |
| 6,780,651 B2 | | 8/2004 | Douglas et al. |
| 6,806,223 B2 | | 10/2004 | Jensen |
| 6,924,153 B1 | | 8/2005 | Boehringer et al. |
| 6,949,246 B2 | | 9/2005 | Reed et al. |
| 6,949,345 B1 | | 9/2005 | Menozzi et al. |
| 7,011,940 B1 | * | 3/2006 | Sompuram et al. ............ 435/4 |
| 2001/0012888 A1 | | 8/2001 | Alderson et al. |
| 2002/0009459 A1 | | 1/2002 | Reed et al. |
| 2002/0137200 A1 | | 9/2002 | Takahashi et al. |
| 2003/0027774 A1 | | 2/2003 | Hendrickson et al. |
| 2003/0135026 A1 | | 7/2003 | Reed et al. |
| 2003/0143243 A1 | | 7/2003 | Reed et al. |
| 2003/0147911 A1 | | 8/2003 | Reed et al. |
| 2004/0013677 A1 | | 1/2004 | Skeiky et al. |
| 2005/0136069 A1 | | 6/2005 | Reed et al. |
| 2005/0181419 A1 | | 8/2005 | Reed et al. |

FOREIGN PATENT DOCUMENTS

| | | |
|---|---|---|
| GB | 2345133 A | 6/2000 |
| JP | 6027103 A | 2/1994 |
| JP | 6273419 A | 9/1994 |
| JP | 8285849 A | 1/1996 |
| WO | 89/11100 | 11/1989 |
| WO | 95/18624 | 7/1995 |
| WO | 96/21863 | 7/1996 |
| WO | 97/44463 | 11/1997 |
| WO | 97/44464 | 11/1997 |
| WO | 98/12562 | 3/1998 |
| WO | 98/16645 | 4/1998 |
| WO | 98/30699 | 7/1998 |
| WO | 98/53075 | 11/1998 |
| WO | 98/53076 | 11/1998 |
| WO | 99/51748 | 10/1999 |
| WO | WO 01/92886 A1 | 6/2001 |

OTHER PUBLICATIONS

Helena Enroth et al., Diagnostic Accuracy of a Rapid Whole-Blood Test for Detection of *Helicobacter pylori*, Journal of Clinical Microbiology, Oct. 1997, p. 2695-2697.

Margaret A. Stone et al., Near patient testing for *Helicobcter pylori*: a detailed evaluation of the Cortecs Helisal Rapid Blood Test, European Journal of Gastoenterology & Hepatology, 1997, vol. 9 No. 3.

Ralph E. Giles et al., Simple/Rapid Test Devices for Anti-HIV Screening: Do They Come Up to the Mark?, Journal of Medical Virology, 1999, 59:104-109.

Japan Patent Office, Office Action for Japanese Patent Application No. 538233/2007, Aug. 9, 2011.

\* cited by examiner

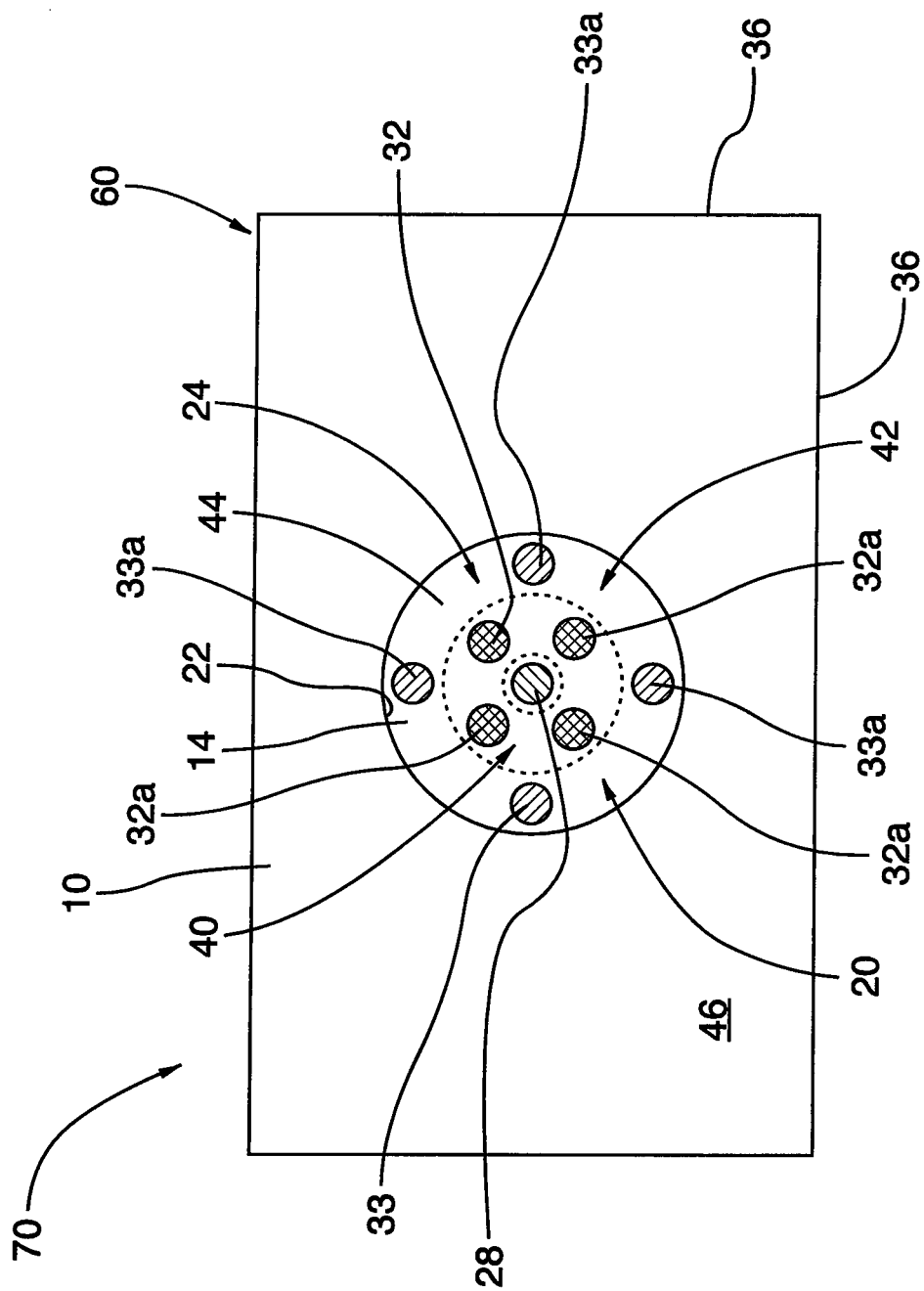

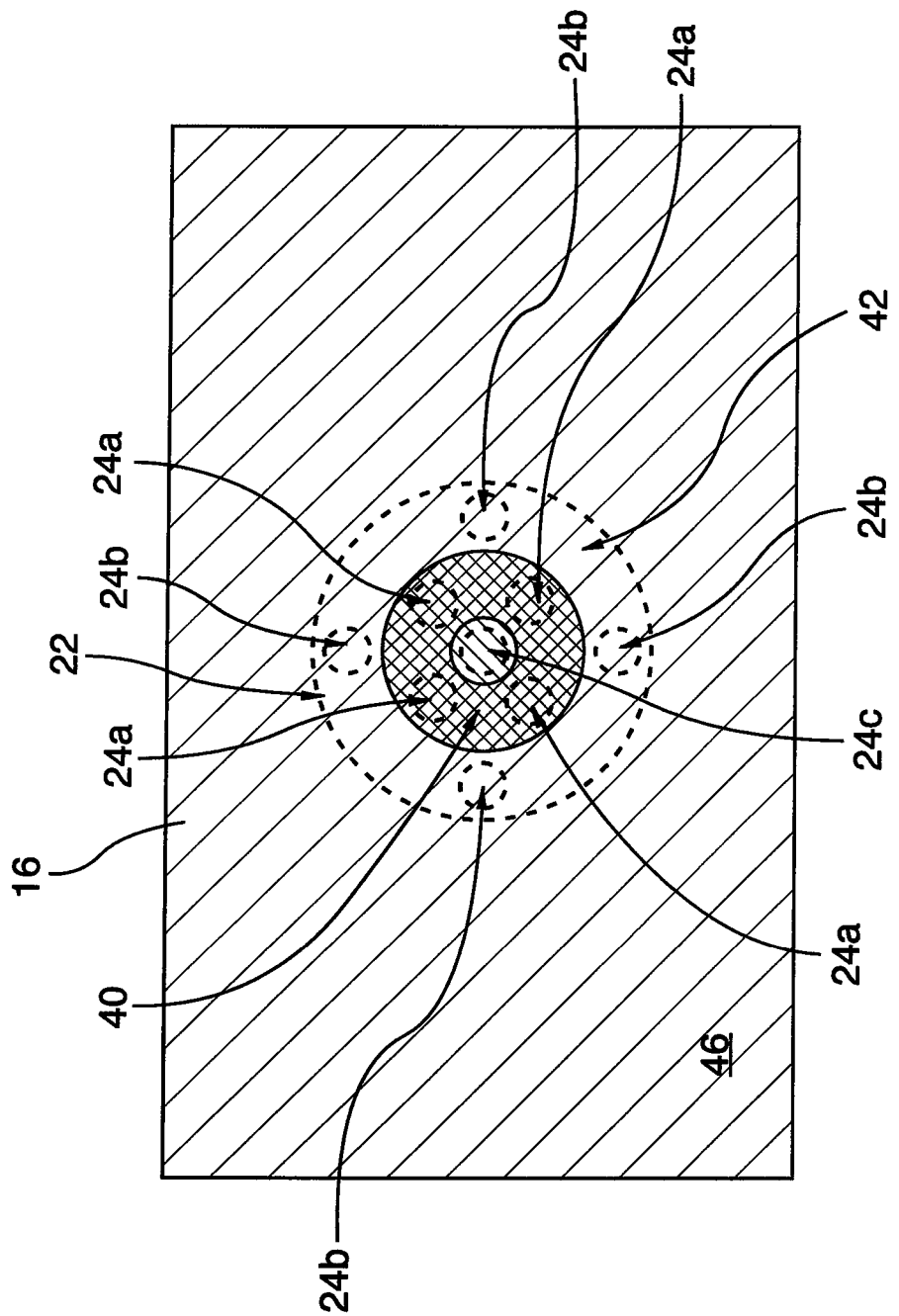

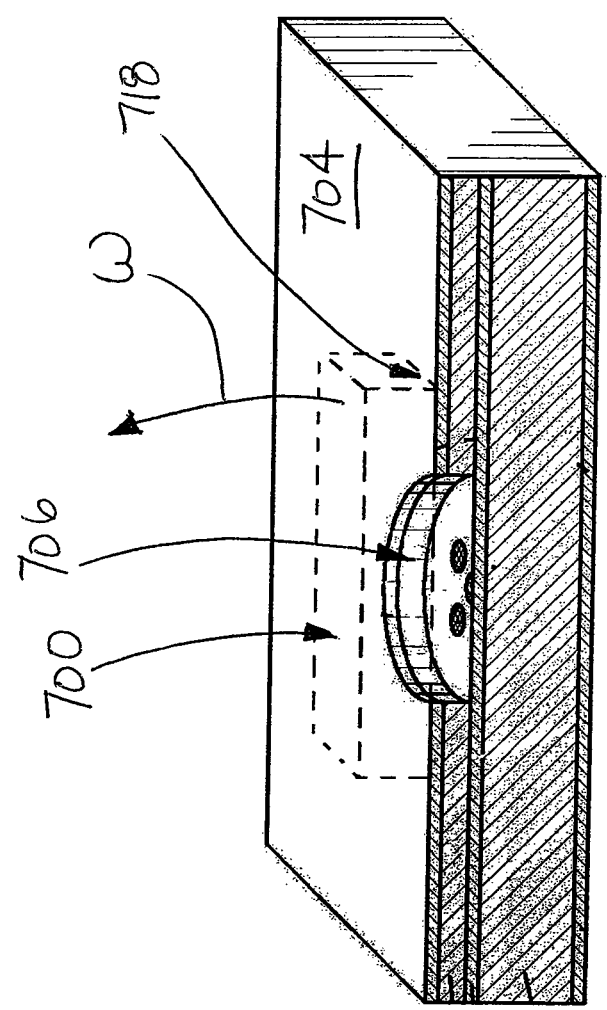

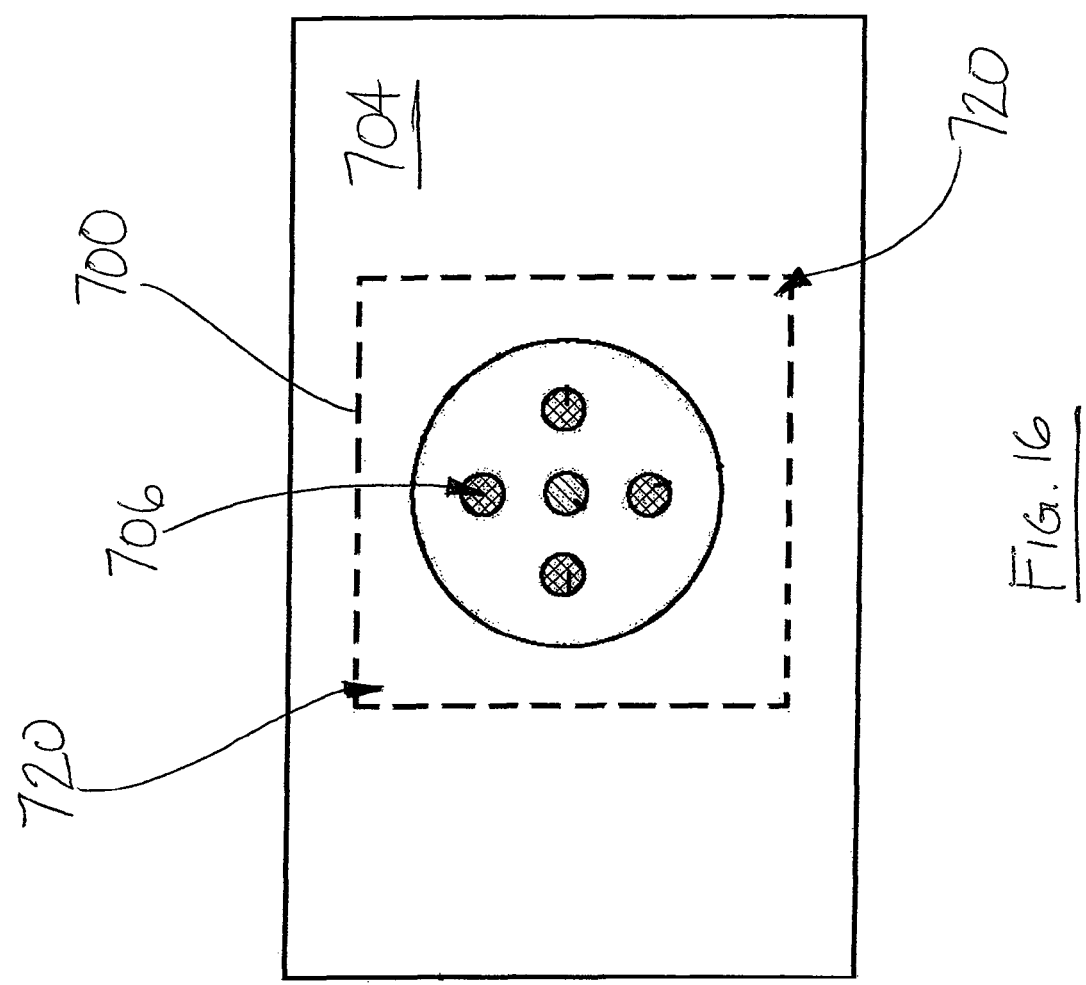

DISPOSABLE IMMUNODIAGNOSTIC TEST SYSTEM

FIELD OF THE INVENTION

The invention relates to the field of immunodiagnostic test systems, kits, and devices, and more particularly to an immunodiagnostic test system for testing for the presence of marker proteins and/or analytes in a test sample.

BACKGROUND OF THE INVENTION

Various diagnostic testing methods and kits have been used in clinical environments, such as, for example, immunochromatographic assays, multi-immunoassay diagnostic systems that test for the presence of antigens and/or antibodies, assay sample analyzing devices, and rapid immunoassay test strips. Other rapid assay test devices and methodologies may be known to a greater or lesser extent in the art, and these may be categorized into one of a number of formats, depending on whether the sample being tested flows through the device, and possibly also depending on the manner and/or direction of any such flow. For example, test devices may have a dipstick, a flow-through, and/or a lateral flow format.

There is, however, a continuing need for a test device that may provide quicker and more accurate test results, that may not require the purchase of additional specialized equipment nor the supplemental training of already highly qualified testing personnel, and/or that may enable a single analyte sample to be tested on a substantially contemporaneous basis for the presence of any of a plurality of causative agents. There is likewise a need for an immunodiagnostic test system, kit and/or device (which may, hereinafter, simply be referred to as an "immunodiagnostic test system") that is effective and simple to use, and may be quickly administered.

There is also a pressing need—one that has not been adequately addressed by previous devices—for a test system that might be readily used and/or disposed of at the "point of care" and/or "in the field" (that is, outside of traditional clinical environments whether, for example, as part of a temporary outreach program, emergency response effort, in a field hospital, and/or in an actual field tending to a plant crop or a herd of afflicted livestock).

Additionally, there is a need for a test system that may be manufactured and/or assembled in the field and/or in a manufacturing facility that is specifically designed for that purpose. There is also a need for such a system that might also involve lower production and packaging costs.

A further need exists for a test system that may be selectively adaptable to provide either qualitative and/or quantitative results, depending on user preferences and/or the nature of the test to be conducted.

Previously, the disposal of "point of care" immunodiagnostic systems may have posed a significant difficulty or problem for those workers given this duty. In the past, such a device (that had been potentially contaminated device following its use) would typically have been sent to a landfill for disposal, thus giving rise to a whole host of environmental costs and concerns, including the potential that, over time, contaminants from the device might seep into the landfill and its surrounding regions. Landfill disposal of some currently marketed immunodiagnostic test systems has heretofore been substantially necessitated by the fact that such systems have typically been primarily composed of materials (such as plastic) that cannot be safely burned or incinerated without generating harmful and/or toxic fumes. The disposal of test systems in landfills has also typically involved additional transportation and disposal costs and efforts. Partially because of this last fact, field workers have been required to carry portable waste containers suited to securely transporting and disposing of such potentially contaminated test systems. Such waste procedures may have involved sterile glassware, plastic ware, laboratory ware, and the like, as well as correspondingly stringent sterilizing and handling regimes. Accordingly, there is a continuing and acutely felt need for a test system that might be readily disposed of in a simple yet ecologically responsible manner, such as, for example, by incineration over an open fire.

There is also a need for a test system that may be selectively adaptable to detect for viral, fungal, bacterial, and/or vector induced infections, any or all of these tests possibly being performed using a single sample.

In addition to all of the foregoing, there is a need for a test system that provides visually discernable test results and/or results within a relatively short period of time, such as, for example, within sixty to ninety seconds.

Accordingly, it is an object of the invention to obviate, mitigate, and/or address one or more of the above mentioned needs, shortcomings and/or disadvantages associated with the prior art.

Additionally, there is a need for a test system that may be used with solid and/or liquid test samples, that enables a substantially clear result which is unobstructed and/or unclouded by non-analyte particulate matter that may be present in the test samples.

SUMMARY OF THE INVENTION

In accordance with the present invention, there is disclosed a disposable immunodiagnostic test system for testing for the presence of marker proteins in a liquid sample analyte. The test system includes a substantially planar passage layer comprised of a first material having a substantially non-porous structure that is shaped so as to define at least one aperture therethrough. The test system also includes a protein layer comprised of a second material that is adapted to enable, in an operative configuration, substantial immobilization of combinable proteins thereon. The protein layer has a substantially porous structure so as to enable a portion of the liquid sample analyte to pass substantially therethrough. The protein layer is in intimate contacting relation with the passage layer so as to define an active surface area on the protein layer that is substantially adjacent to, and substantially aligned with, the aperture of the passage layer. The test system also includes an absorbent layer comprised of a third material that enables absorption of at least a portion of the liquid sample analyte. The absorbent layer is in intimate contacting relation with the protein layer. In the operative configuration, the combinable proteins are substantially immobilized on the protein layer as aforesaid, and the liquid sample analyte is introduced onto the protein layer through the at least one aperture of the passage layer. In a positive result configuration, the marker proteins are bound to the combinable proteins and substantially immobilized relative to the protein layer. In a negative result configuration, at least a portion of the liquid sample analyte passes substantially through the protein layer.

According to a further aspect of the invention, the first material, the second material, and the third material are constructed of at least one combustible material that produces non-toxic by-products upon incineration.

According to an aspect of a preferred embodiment of the invention, the test system may also preferably comprise a reagent that, in the positive result configuration, is operatively bound to the marker proteins that are substantially immobilized relative to the protein layer.

According to an aspect of one preferred embodiment of the invention, the reagent may comprise a visually tagging substance that operatively provides a colored indicium of the positive result configuration.

According to an aspect of another preferred embodiment of the invention, the reagent may comprise a protein enzyme conjugate substance. In this embodiment, the test system may preferably further comprise an enzyme substrate substance that is operatively bound to the protein enzyme conjugate substance in the positive result configuration, and that may preferably operatively display a colored indicium in the positive result configuration.

According to an aspect of one preferred embodiment of the invention, at least a visible portion of the active surface area may be viewable through the aperture of the passage layer.

According to an aspect of one preferred embodiment of the invention, the test system may preferably further comprise at least one sealant substantially juxtaposed between the passage layer and the protein layer, and between the protein layer and the absorbent layer.

According to a further aspect of a preferred embodiment of the invention, the visible portion of the active surface area may preferably comprise a first test surface area, with the combinable proteins preferably being substantially immobilized thereon in the operative configuration. The visible portion of the active surface area may preferably further comprise a procedural control surface area. The procedural control surface area may preferably be adapted to display a control reading both in the positive result configuration and in the negative result configuration, so as to operatively confirm that the test system has been used properly.

According to an additional aspect of a preferred embodiment of the invention, the test system may preferably further comprise a housing substantially encapsulating the passage layer, the protein layer, and the absorbent layer. A lower housing portion of the housing is in intimate contacting relation with the absorbent layer. An upper housing portion of the housing is in intimate contacting relation with the passage layer. The upper housing portion is shaped so as to define at least one housing aperture therethrough. The housing aperture is substantially aligned in operative fluid communicating relation with the at least one aperture of the passage layer.

According to a further aspect of a preferred embodiment of the invention, the housing may preferably be constructed of the aforesaid at least one combustible material.

According to an aspect of one preferred embodiment of the invention, the housing may preferably be comprised of a housing material having a substantially non-porous housing structure.

According to an aspect of one preferred embodiment of the invention, at least one sealant may preferably be substantially juxtaposed between the upper housing portion and the passage layer, and between the lower housing portion and the absorbent layer.

According to a further aspect of one of the preferred embodiments of the invention, the housing may preferably comprise an exterior surface portion with at least one labeling indicium marked thereon. The exterior surface portion may preferably be provided on the upper housing portion.

According to one aspect of the invention, the combinable proteins may preferably, but not necessarily, comprise proteins adapted to be bound to fungal marker proteins, viral marker proteins, bacterial marker proteins, vector-induced marker proteins, plant marker proteins, and/or native proteins biosynthesizable by substantially healthy cells in at least one of the liquid sample analyte and a species furnishing same.

According to an aspect of one of the preferred embodiments of the invention, the visible portion of the active surface area may preferably further comprise a second test surface area. In the operative configuration, second combinable proteins are substantially immobilized on the second test surface area. In the positive result configuration, the marker proteins are bound to the second combinable proteins and substantially immobilized relative to the protein layer.

According to a further aspect of this preferred embodiment of the invention, the visible portion of the active surface area may preferably further comprise a supplemental first test surface area and a supplemental second test surface area. In the operative configuration, the combinable proteins are preferably, but not necessarily, substantially immobilized on each of the first test surface area and the supplemental first test surface area. In the operative configuration, the second combinable proteins are preferably, but not necessarily, substantially immobilized on each of the second test surface area and the supplemental second test surface area.

According to an aspect of one preferred embodiment of the invention, a substantially higher concentration of the combinable proteins are substantially immobilized on the supplemental first test surface area relative to a concentration of the combinable proteins on the first test surface area.

According to an aspect of one preferred embodiment of the invention, the first test surface area and the supplemental first test surface area may together preferably, but not necessarily, notionally define a substantially planar first test ring, with each of the first test surface area and the supplemental first test surface area notionally situated therewithin. Likewise, the second test surface area and the supplemental second test surface area may together preferably, but not necessarily, notionally define a substantially planar second test ring, with each of the second test surface area and the supplemental second test surface area notionally situated therewithin. The second test ring may preferably, but not necessarily, substantially circumscribe the first test ring.

Likewise, according to an aspect of one preferred embodiment of the invention, the first test ring may preferably, but not necessarily, substantially circumscribe the procedural control surface area.

According to an aspect of one preferred embodiment of the invention, the at least one aperture of the passage layer may preferably, but not necessarily, comprise at least two apertures. An upper surface of the passage layer may preferably, but not necessarily, be shaped so as to define a concave portion substantially adjacent to the at least two apertures and substantially aligned with the housing aperture.

According to an aspect of another preferred embodiment of the invention, an upper surface of the protein layer may preferably, but not necessarily, be shaped so as to define a concave portion. The concave portion is preferably, but not necessarily, substantially adjacent to the visible portion of the active surface area and substantially aligned with the aperture of the passage layer.

According to another embodiment of the invention, the test system may be used to test for the presence of marker proteins and/or analytes in a sample. The test system may include, without limitation, a substantially planar passage layer that has a substantially non-porous structure that defines at least one aperture therethrough. The test system may also include, without limitation, a protein layer with combinable proteins operatively immobilized thereon. The protein layer has a substantially porous structure that may operatively enable a liquid portion of the sample (if the sample inherently includes a liquid portion, and/or the combined liquid sample—which is specified in greater detail hereinbelow) to pass therethrough. The protein layer is in intimate contacting relation with the passage layer. An active surface area of the protein layer may preferably, but need not necessarily, be adjacent to, and/or aligned with, the aperture of the passage layer. The test system may also include, without limitation, an absorbent layer operatively enabling absorption of at least the liquid portion of the sample (if the sample inherently includes a liquid portion, and/or the aforementioned combined liquid sample which is to be specified in greater detail hereinbelow). The absorbent layer is in intimate contacting relation with the protein layer. The test system may also include, without limitation, an optional housing which may or may not be present as part of the test system. The housing (if present) may substantially encapsulate the passage layer, the protein layer, and the absorbent layer. The housing (if present) may preferably, but need not necessarily, have a substantially non-porous structure and/or be in intimate contacting relation with the absorbent layer and/or with said passage layer. The housing (if present) may or may not include an upper portion which may preferably, but need not necessarily, define at least one housing aperture. The at least one housing aperture (if present) may preferably, but need not necessarily, be substantially aligned with the at least one aperture of the passage layer. Preferably, in a positive result configuration, the marker proteins may be bound to the combinable proteins and immobilized relative to the protein layer. In a negative result configuration, at least a portion of the liquid portion (if present) of the sample (and/or at least a portion of the aforementioned combined liquid sample which is to be specified in greater detail hereinbelow) may preferably, but need not necessarily pass substantially through the protein layer.

Now, in addition to, and/or in contradistinction from, any other portions and/or embodiments of the test system which are described elsewhere herein, according to one aspect of the invention, the test system may include a wash structure that is pre-formed in and/or secured to, and/or selectively formable in and/or securable to, at least one upper outer surface of the test kit. The upper outer surface may be a passage layer surface and/or a housing surface (if present). Preferably, the wash structure is substantially adjacent to and/or aligned with a test aperture of the system. The test aperture is defined by the at least one aperture in the passage layer and/or by the housing aperture (if present). According to this aspect of the invention, in the operative configuration, the sample may preferably, but need not necessarily, be combined with a suitable wash solution on, and/or in, the wash structure to form a combined liquid sample. The combined liquid sample may preferably, but need not necessarily, be then caused to flow, possibly under the influence of gravity, from the wash structure to the test aperture. In this manner, the combined liquid sample may preferably, but need not necessarily, be introduced onto the protein layer through the at least one aperture of the passage layer.

In addition to, and/or in contradistinction from, any other portions and/or embodiments of the test system which are described elsewhere herein, according to one aspect of the invention, the test system may include a mixing bowl that is pre-formed, and/or selectively formable, in at least one upper outer surface of the test kit. The bowl is formed, and/or formable, substantially adjacent to the test aperture. In the operative configuration, the sample may preferably, but need not necessarily, be combined with a suitable wash solution in the mixing bowl to form a combined liquid sample. The combined liquid sample may preferably, but need not necessarily, be then caused to flow, by tipping and/or inclining the test kit and/or under the influence of gravity, from the bowl to the test aperture. In this manner, the combined liquid sample may preferably, but need not necessarily be, introduced onto the protein layer through the at least one aperture of the passage layer.

According to one aspect of a preferred embodiment of the invention, the upper outer surface of the test kit may preferably, but need not necessarily, be provided with at least one pre-formed, and/or selectively formable, channel that runs between the mixing bowl and the test aperture. The combined liquid sample may preferably, but need not necessarily, flow from the bowl to the test aperture substantially within the channel.

According to another aspect of a preferred embodiment of the invention, the at least one channel may preferably, but need not necessarily, comprise a plurality of channels running between the mixing bowl and the test aperture.

According to another aspect of a preferred embodiment of the invention, the combined liquid sample in each one of the plurality of channels may preferably, but need not necessarily, traverse substantially the same distance between the mixing bowl and the test aperture as the combined liquid sample in each other one of the plurality of channels.

According to one aspect of another preferred embodiment of the invention, one or more of the mixing bowl and the channel(s), if present, may preferably, but need not necessarily, be selectively formable by depressing at least one frangible area that is preferably, but not necessarily, provided on the upper outer surface of the test kit.

According to one aspect of another preferred embodiment of the invention, the upper outer surface of the test kit may preferably, but need not necessarily, be marked with at least one local indicium (such as, for example and without limitation, a dotted outline)—preferably, but not necessarily, to indicate the location of the frangible area.

According to one aspect of another preferred embodiment of the invention, the upper outer surface of the test kit may preferably, but need not necessarily, be marked with at least one instructional indicium (such as, for example and without limitation, (i) the letters "A" and "B" positioned adjacent to the mixing bowl and test aperture, respectively; (ii) the numbers "1" and "2" positioned adjacent to the mixing bowl and test aperture, respectively; and/or (iii) an arrow pointing from the mixing bowl to the test aperture)—preferably, but not necessarily, to suggest one preferable use of the mixing bowl, in order, before use of the test aperture.

According to one aspect of another preferred embodiment of the invention, the mixing bowl may preferably, but need not necessarily, be sized to accommodate a volume of the combined liquid sample which is substantially greater than, or substantially equal to, the volume of the combined liquid sample which may preferably be accommodated within the test aperture.

In addition to, and/or in contradistinction from, any other portions and/or embodiments of the test system which are described elsewhere herein, according to one aspect of the invention, the test system may include a wash tablet that is secured, and/or selectively securable, to at least one upper outer surface of the test kit. The wash tablet may preferably, but need not necessarily, be secured and/or securable, in substantially overlying relation, above the test aperture. In the operative configuration, the sample may preferably, but need not necessarily, be combined with a suitable wash solution on and/or in the wash tablet to form the combined liquid sample. The combined liquid sample may preferably, but need not necessarily, then be caused to flow, by a wicking effect and/or under the influence of gravity, from the wash tablet to the test aperture. In this manner, the combined liquid sample may preferably, but need not necessarily, be introduced onto the protein layer through the at least one aperture of the passage layer.

According to one aspect of a preferred embodiment of the invention, the wash solution may preferably, but need not necessarily, be introduced into the tablet before the sample.

According to one aspect of another preferred embodiment of the invention, the tablet may preferably, but need not necessarily, be saturated with the wash solution before the sample is introduced into the tablet.

According to one aspect of another preferred embodiment of the invention, the wash tablet may preferably, but need not necessarily, be constructed—whether in part or entirely—from a material that is selected from the group which includes, without limitation, glass fiber materials (such as, for example and without limitation, spun fiberglass), other synthetic fiber materials (such as, for example and without limitation, nylon), paper materials (such as, for example and without limitation, cellular acetate, loose cardboard materials, paper towels), and/or sponge materials (preferably, but not necessarily, of a specified minimum porosity).

According to one aspect of another preferred embodiment of the invention, the wash tablet may preferably, but need not necessarily, be constructed—whether in part or entirely—from a first material that is operatively impregnated with a second material (such as, for example and without limitation, a lectin) that binds to cellular, lipid and/or particulate portions of the sample. The first and second materials may preferably, but need not necessarily, also allow substantially unimpeded passage of the analytes therethrough.

According to one aspect of another preferred embodiment of the invention, the wash tablet may preferably, but need not necessarily, be secured and/or selectively securable to the upper outer surface of the test kit by securing means. The securing means may, for example and without limitation, be a tape and/or an adhesive.

According to another aspect of a preferred embodiment of the invention, the securing means may preferably, but need not necessarily, be applied substantially adjacent to corners and/or edges of the wash tablet.

According to another aspect of another embodiment of the invention, the securing means may preferably, but need not necessarily, be tape (such as, for example and without limitation, scotch tape) that may, but need not necessarily, be applied over top of the wash tablet.

According to one aspect of another preferred embodiment of the invention, after the combined liquid sample is introduced onto the protein layer, the wash tablet may preferably, but need not necessarily, be peeled back (and/or otherwise removed) from the test aperture (and/or otherwise rendered observably non-obstructing) to reveal the positive result configuration and/or the negative result configuration.

According to one aspect of another preferred embodiment of the invention, one or more of the passage layer, the protein layer, the absorbent layer, the housing (if present), the wash structure (if present), and/or the wash tablet (if present) may preferably, but need not necessarily, be constructed of one or more combustible materials. One or more of such combustible materials may preferably, but need not necessarily, produce non-toxic by-products upon incineration.

According to one aspect of another preferred embodiment of the invention, one or more of the passage layer, the protein layer, the absorbent layer, the housing (if present), the wash structure (if present), and/or the wash tablet (if present) may preferably, but need not necessarily, be constructed of a densely packed paper material.

Other advantages, features and characteristics of the present invention, as well as methods of operation and functions of the related elements of the structure, and the combination of parts and economies of manufacture, will become more apparent upon consideration of the following detailed description and the appended claims with reference to the accompanying drawings, the latter of which are briefly described hereinbelow.

BRIEF DESCRIPTION OF THE DRAWINGS

The novel features which are believed to be characteristic of a disposable immunodiagnostic test system according to the present invention, as to its structure, organization, use and method of use, together with further objectives and advantages thereof, will be better understood from the following drawings in which at least one presently preferred embodiment of the invention will now be illustrated by way of example. It is expressly understood, however, that the drawings are not necessarily depicted to scale and are for the purpose of illustration and description only. For these and other reasons, it should be appreciated that the drawings are not intended as a definition of the limits of the invention. In the accompanying drawings:

FIG. 4C is a top plan view of a still further preferred embodiment of the test system according to the invention which is similar to that shown in FIG. 2A;

FIG. 4E is a top plan view of the test system of FIG. 2D, showing the protein layer, with the housing and passage layer apertures shown in phantom outline;

FIG. 15 is a top front left cross-sectional perspective view of another preferred embodiment of test system similar to that shown in FIG. 14, shown with adhesive securing means; and FIG. 16 is a top plan view of the test system shown in FIG. 15.

DETAILED DESCRIPTION OF A PREFERRED EMBODIMENT

Figure 5A:
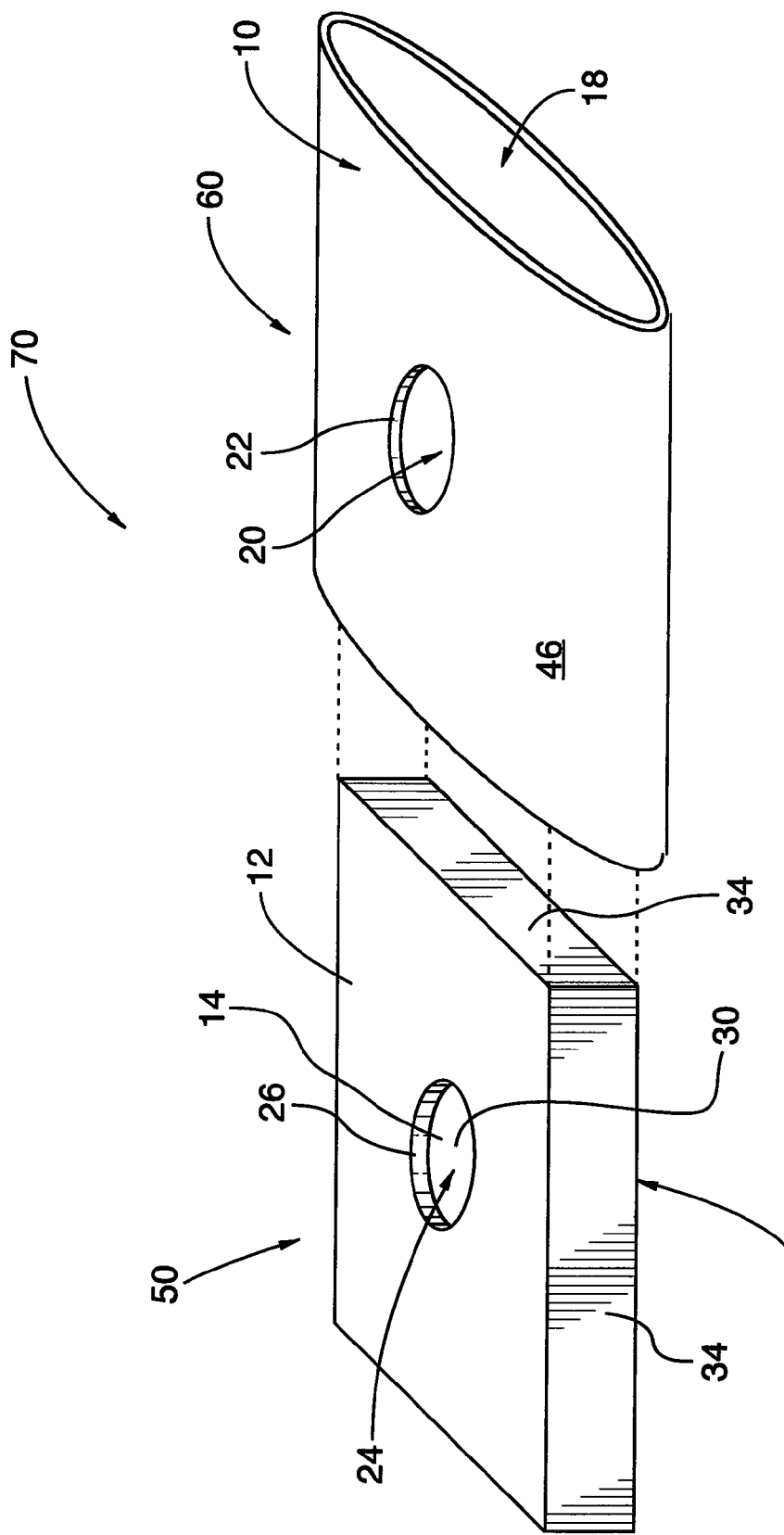
FIG. 5A is a top front left perspective view of still another embodiment of the test system according to the invention, shown in a partially unsealed and exploded configuration.

Referring now to FIGS. 1A, 1B, 5A and 5B of the drawings, there is shown a preferred embodiment of a disposable immunodiagnostic test system 70, according to the invention, for testing for the presence of marker proteins (alternatively referred to as "analytes") in a liquid sample analyte (not shown, but alternatively referred to as a "liquid sample"). As best seen in FIG. 5A, one of the preferred embodiments of the test system 70 includes a combined testing subassembly 50 and a housing 60.

Figure 1A:
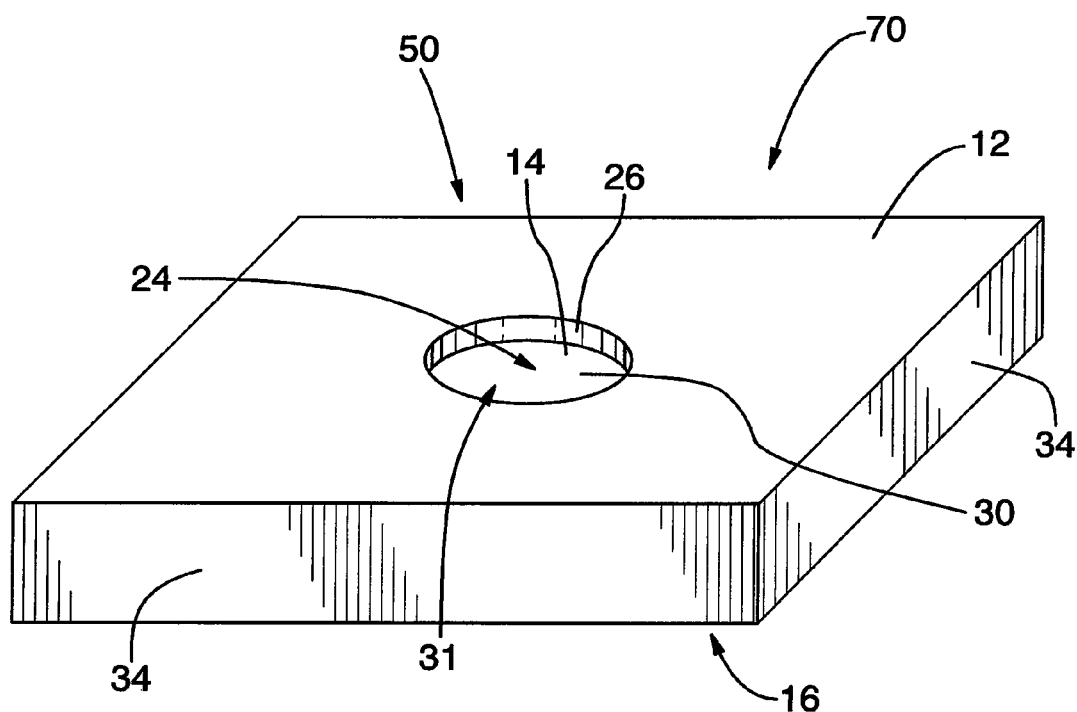
FIG. 1A is top front left perspective view of one preferred embodiment of a disposable immunodiagnostic test system according to the invention.
Figure 1B:
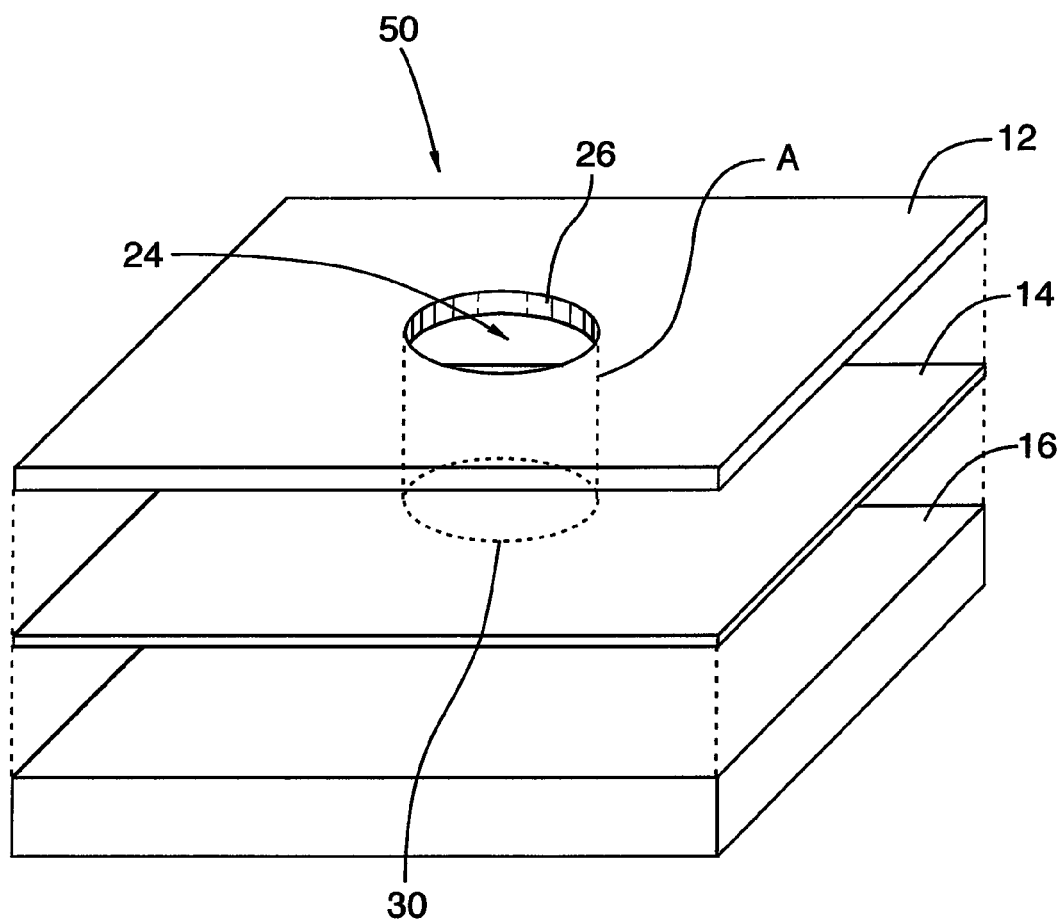
FIG. 1B is a top front left perspective view of the test system of FIG. 1A, shown in an unsealed and exploded configuration with substantially aligning portions thereof shown in phantom outline.

It is also noted that, as best seen in FIGS. 1A and 1B, the test system 70 may simply include the combined testing subassembly 50, without the housing 60.

With further reference to FIG. 1B, the combined testing subassembly 50 will be seen to include a substantially planar passage layer 12, a protein layer 14, and an absorbent layer 16, each of which is preferably constructed of a combustible material that produces non-toxic by-products upon incineration. For this reason, among others, the combined testing subassembly 50 may be easily disposed of in an environmentally responsible manner, such as, for example, by incineration over an open flame.

As aforesaid, the passage layer 12 is substantially planar and has an aperture 24 therethrough that is defined by a corresponding inner edge 26 of the passage layer 12. While the preferred embodiment shown in FIGS. 1A, 1B, 5A and 5B has a single aperture 24 through the passage layer 12, the passage layers of other embodiments (see, for example, FIGS. 2D through 2F which are discussed in further detail hereinbelow) may be provided with more than one aperture 24. The passage layer 12 has a substantially non-porous structure, such that it will preferably have a substantially impermeable, non-sponge, and unwoven nature. The passage layer 12 may preferably, but not necessarily, be constructed of a densely packed paper material, such as cardboard. Other relatively rigid materials, such as, for example, tree bark and/or packed leaf materials, may also be used in the construction of the passage layer 12 according to the invention. Thus, whether as a result of its preferably densely packed nature, the inherent properties of its material of construction, or otherwise, the passage layer 12 preferably provides a measure of rigidity to the test system 70. The passage layer 12 is preferably, though not necessarily, between about 0.2 and 10 millimeters in thickness, with an even more preferred thickness being substantially within the range of between about 2 and 4 millimeters.

As best seen in FIGS. 1A and 1B, the protein layer 14 is in intimate contacting relation with the passage layer 12. The protein layer 14 has an active surface area 30 that is substantially adjacent to said aperture 24 of said passage layer 12, and substantially aligned therewith (as indicated generally by phantom line "A" in FIG. 1B). As best seen in FIG. 1A, at least a portion 31 of the active surface area 30 is preferably visible through the aperture 24.

The protein layer 14 may preferably, though not necessarily, be constructed from nitrocellulose, nylon, and/or acetate, and indeed from any such other material upon which reactant and/or combinable proteins might be bound or immobilized (alternatively, hereinafter "substantially immobilized"). In biotechnology, the terms "immobilization" and "immobilized" may be generally regarded as referring to the technique used for and/or the state of physical or chemical fixation of cells, organelles, enzymes, or other proteins (e.g., monoclonal antibodies) onto a solid support, into a solid matrix, and/or retained by a membrane, among other things, in order to increase their stability and/or for various other purposes. It is thought, though not essential to the working of the test system 70, that nitrocellulose is an effective protein-binding material that might be used in the protein layer 14. Suitable commercially available nitrocellulose membranes may be cast on a supporting thin paper backing and used in the protein layer 14 according to a preferred embodiment the present invention. The protein layer 14 is preferably, though not necessarily, no greater than about 5 millimeters in thickness, with an even more preferred thickness being substantially within the range of between about 0.5 and 2.0 millimeters.

The protein layer 14 has a substantially porous structure, meaning that it is preferably provided with a plurality of pores (not shown) therethrough. In the case of nitrocellulose membranes and some of the other preferred protein layer 14 materials, it is now believed, though not essential to the working of the test system 70, that the provision of larger sized pores in the protein layer 14 will afford correspondingly lower protein binding capabilities and/or capacities. As discussed in further detail hereinbelow, a protein layer 14 having lower protein binding capabilities may lower the sensitivity of any test performed using the system 70. A nitrocellulose protein layer 14 will preferably, though not necessarily, have pore sizes between about 0.1 microns and 25 microns in diameter, with an even more preferred diametrical size being substantially within the range of between about 0.4 and 2.0 microns. It is believed that protein layers 14 having pores (not shown) that are sized substantially within the aforesaid range may afford an improved protein binding capacity.

As best seen in FIG. 1B, the absorbent layer 16 is in intimate contacting relation with the passage layer 12. As its name suggests, the absorbent layer 16 is constructed of an absorbent material that is preferably adapted, depending on the nature of the test to be performed, to take in or absorb at least a portion (more preferably, an excess portion) of the liquid sample analyte that is to be tested. The absorbent layer 16 may preferably be formed from a sponge material, or indeed any other material capable of taking in or absorbing at least a portion of the liquid sample analyte (not shown). For example, the absorbent layer 16 may be constructed from a paper towel and/or an acetate material. The absorbent layer 16 is preferably, though not necessarily, between about 1 and 50 millimeters in thickness, with an even more preferred thickness being substantially within the range of between about 5 and 20 millimeters. Preferably, the absorbent layer 16 will be adapted so that it might absorb and retain three times, or more, of the volume of the liquid sample analyte that is to be administered during a single test.

As aforesaid, the absorbent layer 16 is in intimate contacting relation with the protein layer 14, and the protein layer 14 is in intimate contacting relation with the passage layer 12. Preferably, though not essential to the basic working of the test system 70, the passage layer 12 and the protein layer 14 may be held together in the aforesaid intimate contacting relation with the aid of a sealant (not shown) that is substantially juxtaposed therebetween. Likewise, the protein layer 14 and the passage layer 16 may preferably be held together in the aforesaid intimate contacting relation with the aid of the same or a different sealant (not shown) that is substantially juxtaposed therebetween. Suitable sealants according to the invention may preferably, but not necessarily, include glue and other adhesives, as well as the use of stapling, stitching, and thermal and/or ultrasound sealing methodologies, or indeed any other material or process that is suitable to ensure that the layers 12, 14, 16 are substantially maintained in the aforesaid intimate contacting relation with one another. It is contemplated that, for ease of manufacture, a conventional thermal sealer or glue intended for domestic use may suffice to provide sufficient sealing properties according to the invention.

As best seen in FIGS. 1A and 5A, the combined testing subassembly 50 may preferably also include a subassembly peripheral sealing 34. As shown in FIGS. 1A and 5A, the subassembly peripheral sealing 34 in a preferred embodiment of the test system 70 may securely engage peripheral edge portions of each of the layers 12, 14, 16. The subassembly peripheral sealing 34 may be constructed of the same or a yet different sealant as that which is discussed hereinabove. For example, the subassembly peripheral sealing 34 may consist of an adhesive material that may be adhered to the peripheral edge portions of the layers 12, 14, 16. In addition to the aforesaid sealants and sealing methodologies, the subassembly peripheral sealing 34 may alternately be constructed of any material or indeed in a form that provides physical compression of the layers 12, 14, 16 (possibly substantially adjacent to their peripheral edge portions) to ensure that they are maintained in intimate contacting relation with one another. For example, the subassembly peripheral sealing 34 may consist of a clamping member (not shown) that engages the peripheral edge portion of the passage layer 12 and the absorbent layer 16 so as to apply a compressive force to all three layers 12, 14, 16 in intimate contacting relation with one another.

Figure 5B:
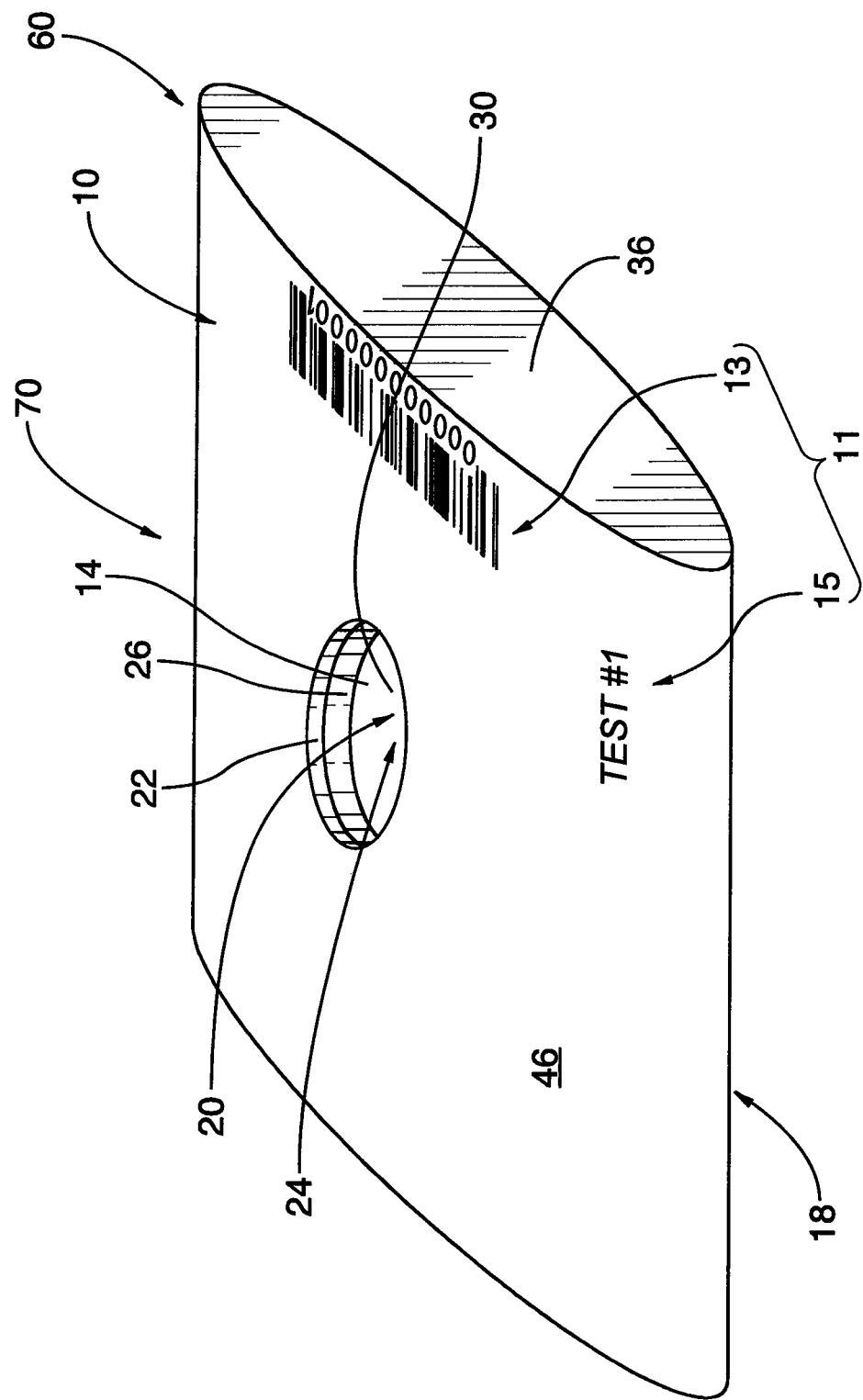
FIG. 5B is a top front left perspective view of the test system of FIG. 5A.

As best seen in FIGS. 5A and 5B, the housing 60 substantially encapsulates the passage layer 12, the protein layer 14, and the absorbent layer 16, as they may together be preferably, but not necessarily, assembled to form the combined testing subassembly 50. The housing 60 may preferably include an upper housing portion 10 and a lower housing portion 18. The upper housing portion 10 and the lower housing portion 18 may be preferably, but not necessarily, in intimate contacting relation with the passage layer 12 and the absorbent layer 16 respectively. Preferably, the upper housing portion 10 and the passage layer 12 may be held together in the aforesaid intimate contacting relation with the aid of the same or a different sealant (not shown) as that aforesaid, which sealant is substantially juxtaposed therebetween. Likewise, the lower housing portion 18 and the absorbent layer 16 may preferably be held together in the aforesaid intimate contacting relation with the aid of the same or a still different sealant (not shown) that is substantially juxtaposed therebetween.

Figure 2A:
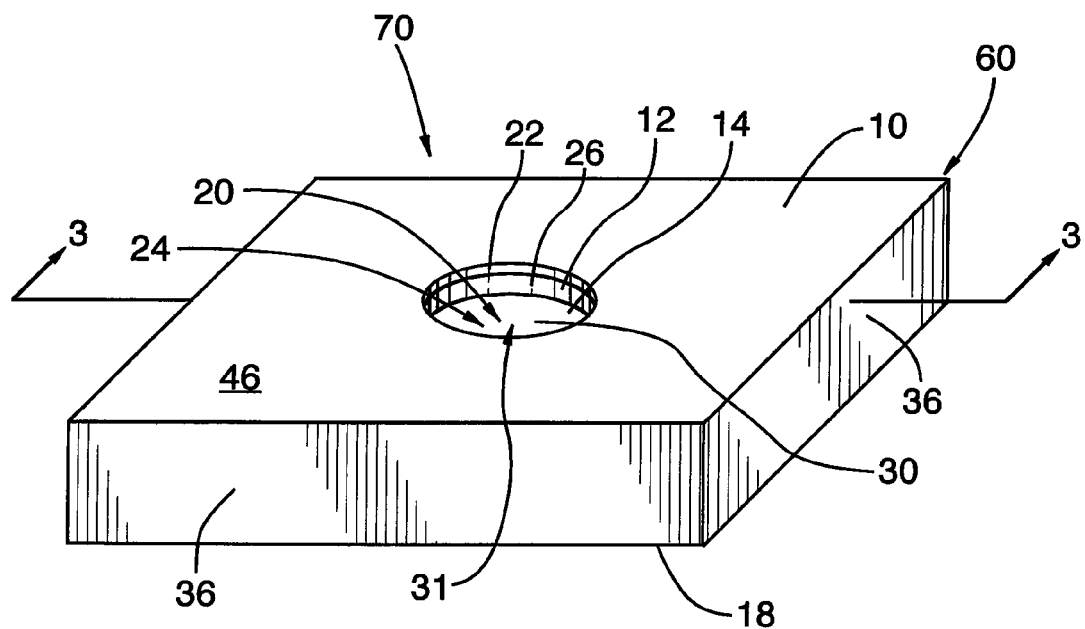
FIG. 2A is a top front left perspective view of another preferred embodiment of a test system according to the invention that includes a housing.
Figure 2D:
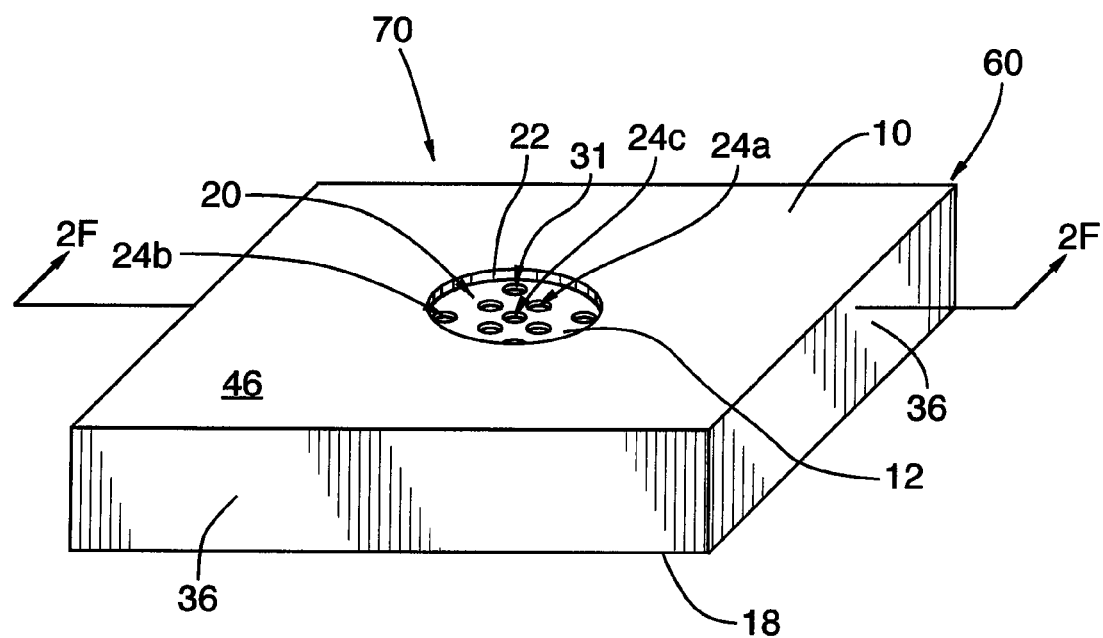
FIG. 2D is a top front left perspective view of a different preferred embodiment of a test system according to the invention that includes a plurality of passage layer apertures.
Figure 3:
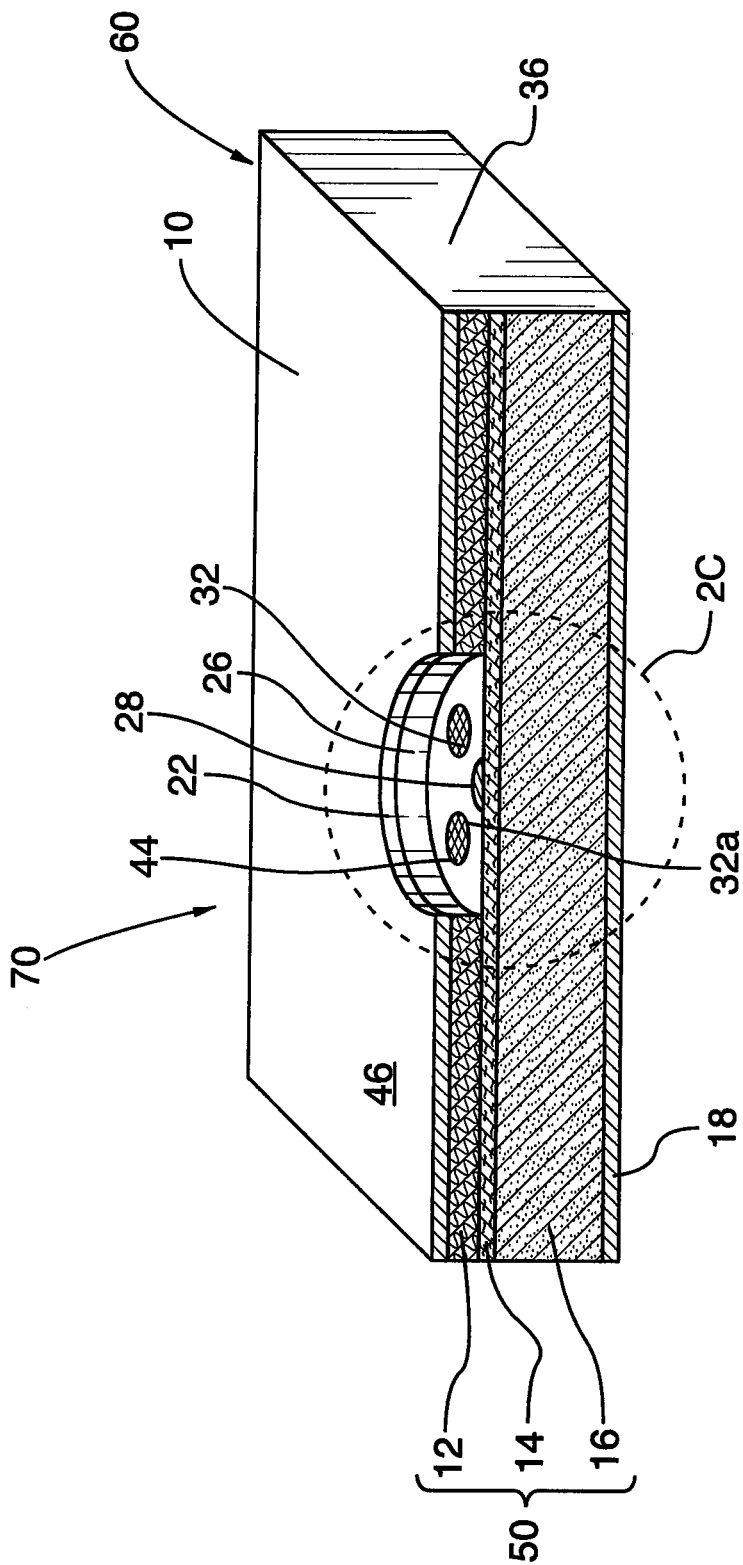
FIG. 3 is a cross-sectional view of the test system of FIG. 2A taken along sight line 3-3.

As best seen in FIG. 5B, the housing 60 may preferably be further provided with housing edge portions 36 that are substantially contiguous with one or more peripheral edges of each of the upper and lower housing portions 10, 18. The housing edge portion 36 in a preferred embodiment of the test system 70 may securely engage peripheral edge portions 34 of the combined testing subassembly 50 (as shown in FIG. 5B), and/or it may engage the peripheral edge portions of each of the layers 12, 14, 16 (as shown in FIGS. 2A, 2D and 3, and discussed in further detail hereinbelow). The housing edge portion 36 may be constructed of the same or a yet different sealant as that which is discussed hereinabove, including any of the alternate sealant materials, methodologies, and/or forms that are mentioned hereinabove with reference to the subassembly peripheral sealing 34, preferably so as to maintain the combined testing subassembly 50 in intimate contacting relation with the housing 60.

As best seen in FIGS. 5A and 5B (and as also shown in FIGS. 2A, 2B, 2D, 2E and 3, wherein other preferred embodiments of the test system 70 are depicted, as may be discussed in further detail hereinbelow), the upper housing portion 10 is provided with a housing aperture 20 therethrough that is defined by a corresponding inner edge 22 of the upper housing portion 10. The housing 60 is preferably constructed from substantially non-porous materials, meaning ones that are preferably substantially impermeable, and/or of a non-absorbing and/or unwoven construction.

All portions of the housing 60 are preferably constructed of materials that produce non-toxic by-products upon incineration, so as to better ensure that the test system 70 might be disposed of in an environmentally responsible manner, such as, for example, by combustion. Paper is one preferred material that may be suitable for the construction of the housing 60. Other like materials may also be used for the housing 60 according to the invention, and such materials might include cloth, nylon, silk, and/or biodegradable membranes. Each of the upper and lower housing portions 10, 18 is preferably, though not necessarily, between about 0.1 and 3 millimeters in thickness, with an even more preferred thickness being substantially within the range of between about 0.2 and 0.4 millimeters.

Preferably, but not necessarily, the dimensions of a single test system 70 adapted for the testing of a single liquid analyte sample will be substantially in the order of about 20 mm×20 mm×10 mm.

As shown in FIG. 5B, the upper housing portion 10 of the housing 60 preferably includes an exterior surface portion 46 with labeling indicia 11 marked thereon. Preferably, the labeling indicia 11 may be visible to the unaided human eye, and may include sequentially numbered barcode indicia 13 and/or text indicia 15. In embodiments not including the housing 60, the labeling indicia 60 may alternately be directly marked (not shown) on an exterior surface portion of the passage layer 12. In either event, the labeling indicia 11 may be marked on the exterior surface portion by way of printing, adhering or being written. Sequentially numbered barcode indicia 13 may preferably, but not necessarily, be provided to enable the tracking of each test system 70 and for other purposes, including, for example, quality control purposes. Similarly, text indicia 15 may include information and data about the disposable immunodiagnostic test system 70 and its intended uses, such as, for example, the name of the intended test, expiration dates, instructions, storage conditions, disposal instructions, and/or the like. It is to be further appreciated that the labeling indicia 11 may also consist of color coding (not shown) to identify each different the type of specific test system 70.

As best seen in FIG. 5A, the test system 70 may be assembled by preferably, but not necessarily, inserting the combined testing subassembly 50 in the hollow housing 60. The housing aperture 20 may preferably be in substantially vertical registration with the underlying aperture 24 in the passage layer 12. The housing 60 may thereafter preferably be sealed at each of its open ends with the housing edge portion 36. As aforesaid, the material from which the housing edge portion 36 is formed may or may not be the same sealant material as that used for the subassembly peripheral sealing 34. In the aforesaid manner, the disposable immunodiagnostic test system 70 (as best seen in FIG. 5B) may preferably, but not necessarily, be completely assembled.

FIGS. 2A through 4E depict alternate preferred embodiments of the test system 70 wherein, as is the case with all of the drawings, similar reference numerals have been used to designate like elements of the present invention, where possible, in the various views for ease of reference. The embodiment of the test system 70 that is shown in FIGS. 2A, 2B, 2C, and 3 is in most respects identical to that which has been discussed hereinabove, save that the upper and lower housing layers 10, 18 each consist of substantially planar and substantially more discrete layer portions than the more pillow-shaped embodiment that is shown in FIGS. 5A and 5B.

Figure 2B:
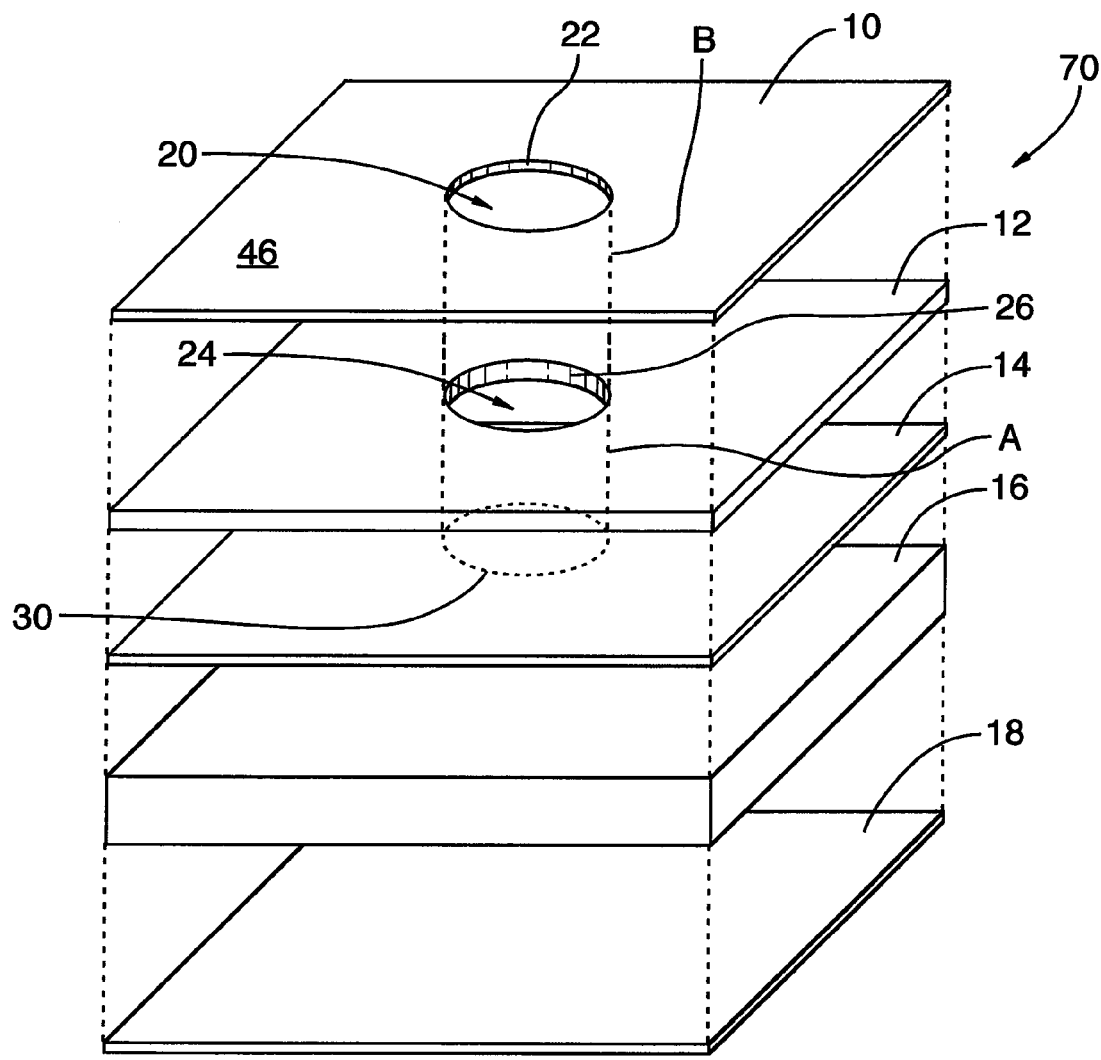
FIG. 2B is a top front left perspective view of the test system of FIG. 2A, shown in the unsealed and exploded configuration.

It may be appreciated from all of the foregoing, and as best seen in FIG. 2B, the housing aperture 20 is substantially aligned with the passage layer aperture 24 (as generally indicated by phantom lines "B" in FIG. 2B).

Figure 2C:
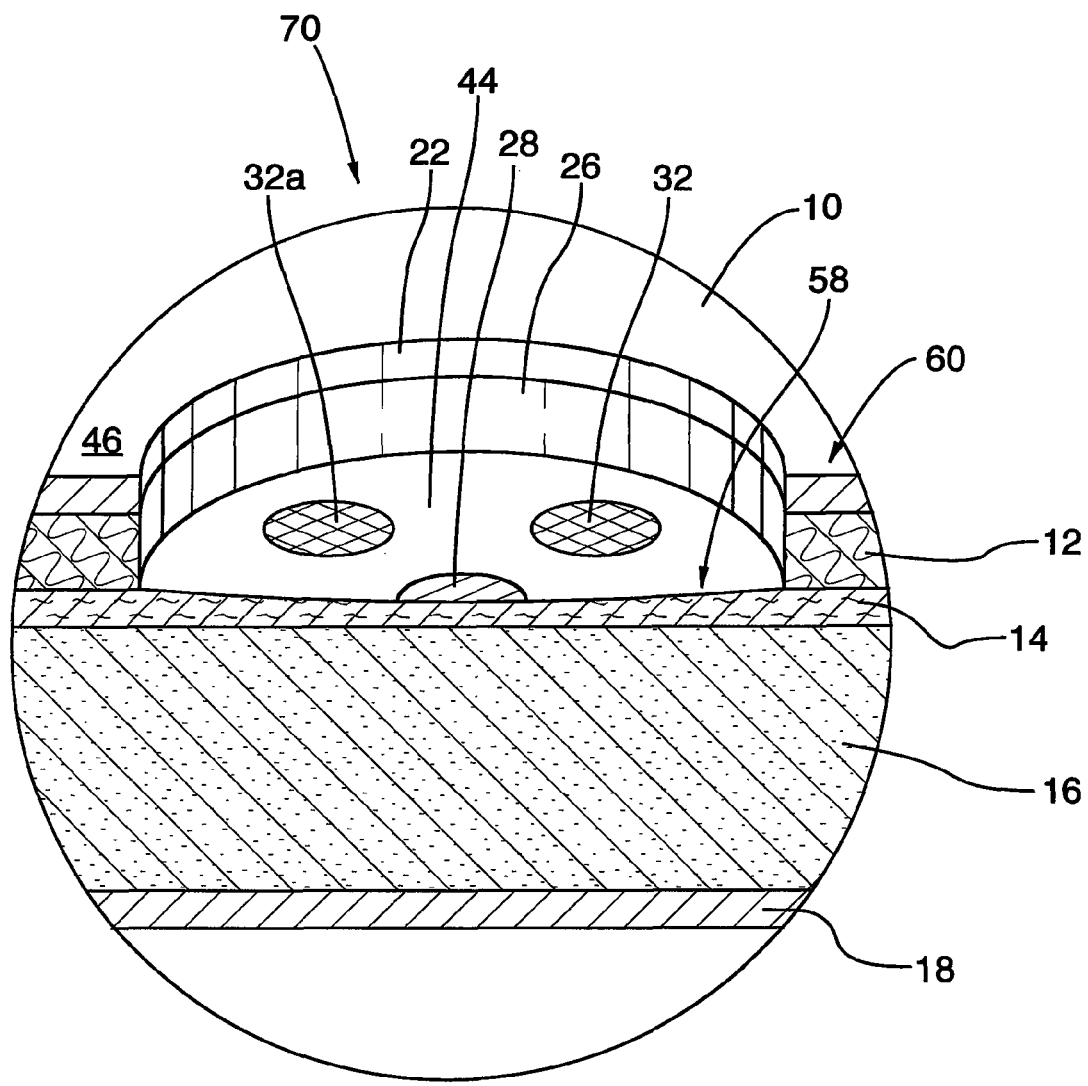
FIG. 2C is an enlarged view of encircled area 2C of FIG. 3, which is discussed hereinbelow.

As best seen in FIG. 2C, the upper surface of the protein layer 14 may preferably, but not necessarily, be shaped so as to define a concave portion 58 that is substantially adjacent to, and substantially aligned with, the inner edges 22, 26 of the upper housing portion 10 and the passage layer 12.

Figure 2E:
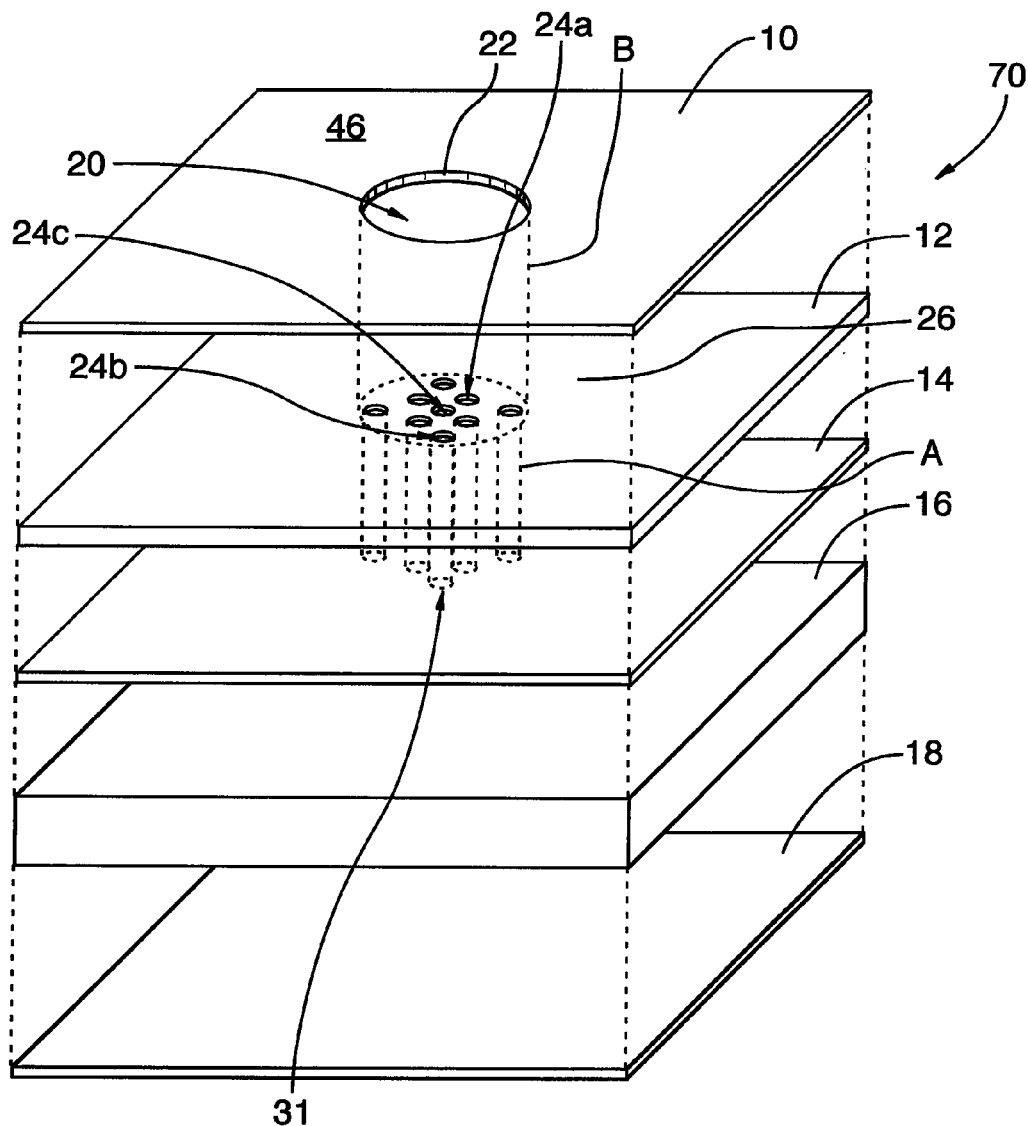
FIG. 2E is a top front left perspective view of the test system of FIG. 2D, shown in the unsealed and exploded configuration.
Figure 2F:
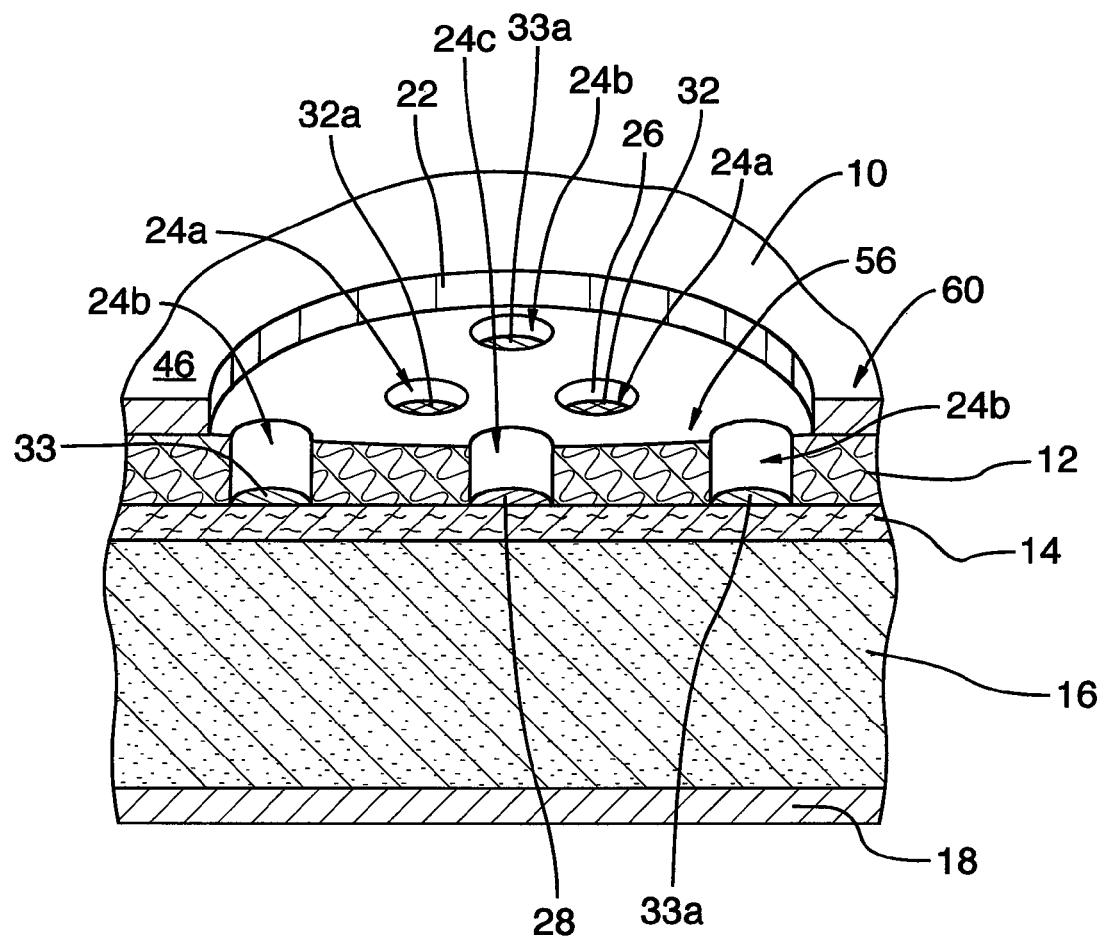
FIG. 2F is an enlarged view, similar to FIG. 2C, of the test system shown in FIG. 2D, along sight line 2F-2F.

With reference to FIGS. 2D through 2F, there is shown an alternate preferred embodiment of the test system 70, wherein the passage layer 12 is provided with first apertures 24a, second apertures 24b, and a control aperture 24c therethrough. As best seen in FIG. 2F, the upper surface of the passage layer 12 may preferably, but not necessarily, be shaped so as to define a concave portion 56 that is substantially adjacent to, and substantially aligned with, the inner edge 22 of the upper housing portion 10.

Figure 6:
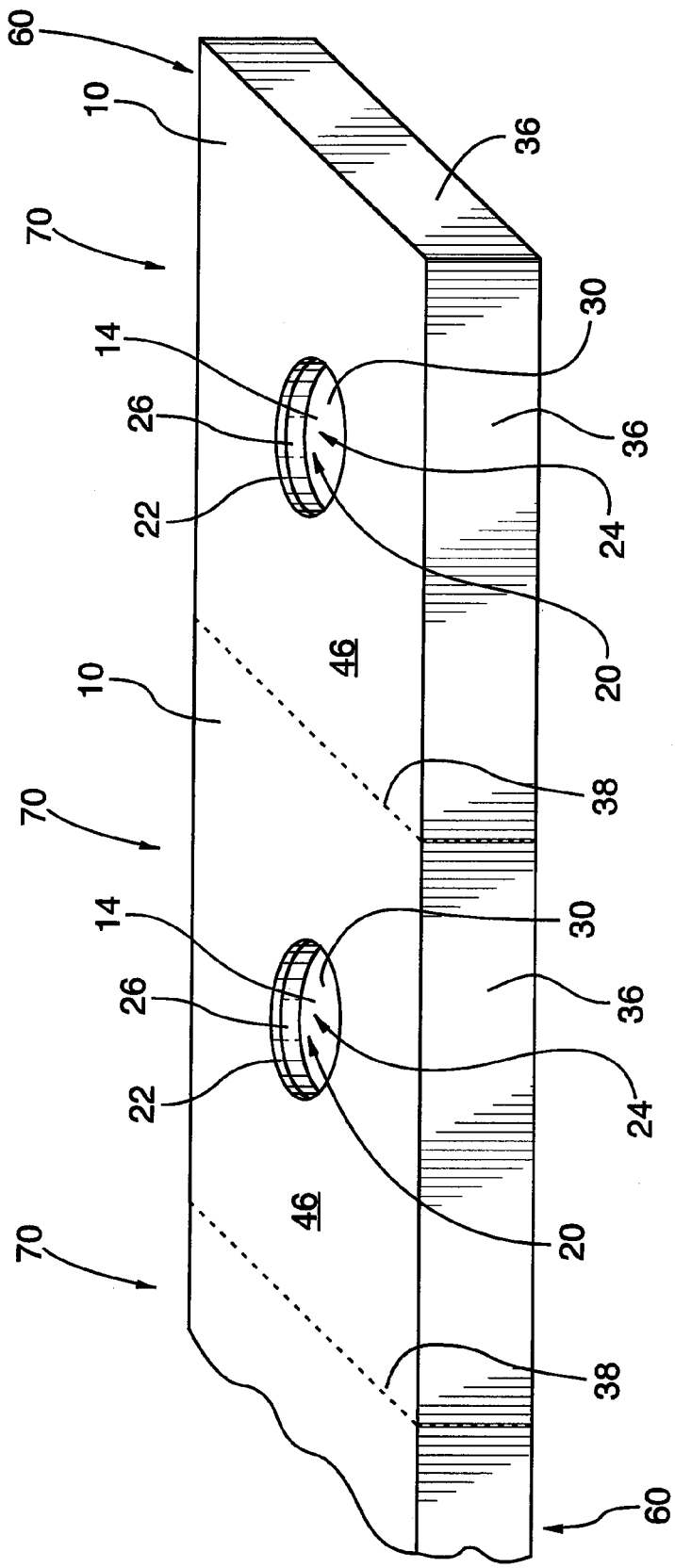
FIG. 6 is a top front left perspective view of a portion of yet another embodiment according to the invention, depicting a plurality of frangible test systems, each similar to that shown in FIG. 2A.
Figure 7:
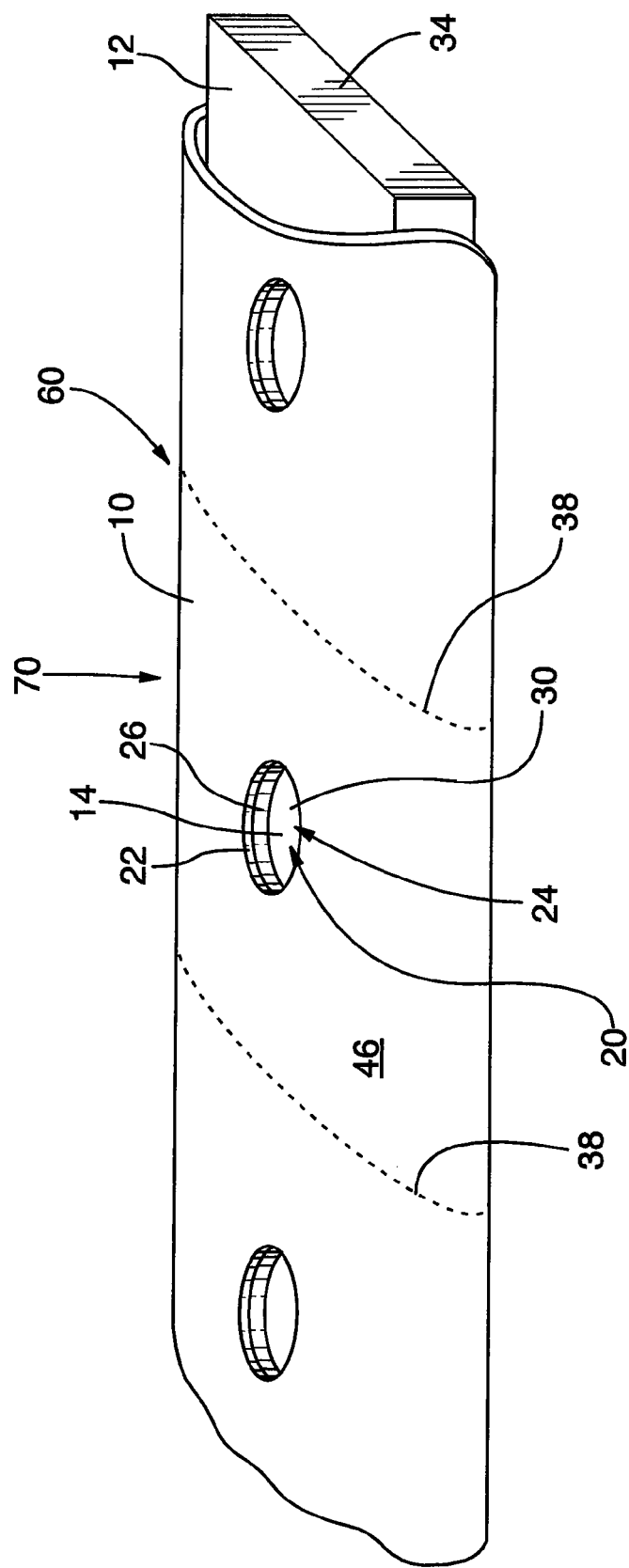
FIG. 7 is a top front left perspective view of a portion of a yet further embodiment according to the invention, depicting a plurality of frangible test systems, each similar to that shown in FIG. 2B.

In accordance with yet further preferred embodiments of the invention which are shown in FIGS. 6 and 7 of the drawings, the disposable immunodiagnostic test system 70 may be provided in a multiple test format. In such embodiments, individual test systems 70 may be arranged in side-by-side removably connected and/or frangible relation by means of tearable housing perforations 38 that may be torn by an end user (not shown), who might determine the number of test systems 70 that are required for any particular or intended use.

The individual test systems 70 that are shown in FIG. 6 may each substantially correspond with those shown elsewhere in FIGS. 2A through 4E. Similarly, the individual test systems 70 that are shown in FIG. 7 may each substantially correspond with those shown in FIGS. 5A and 5B.

Now with reference to FIGS. 8 through 16 of the drawings, and to put it another way, according to some embodiments of the invention, the test system may be used to test for the presence of marker proteins and/or analytes in a sample. The test system may include, without limitation, a substantially planar passage layer that has a substantially non-porous structure that defines at least one aperture therethrough. The test system may also include, without limitation, a protein layer with combinable proteins operatively immobilized thereon. The protein layer has a substantially porous structure that may operatively enable a liquid portion of the sample (if the sample inherently includes a liquid portion, and/or the combined liquid sample (not shown)—which is specified in greater detail hereinbelow) to pass therethrough. The protein layer is in intimate contacting relation with the passage layer. An active surface area of the protein layer may preferably, but need not necessarily, be adjacent to, and/or aligned with, the aperture of the passage layer. The test system may also include, without limitation, an absorbent layer operatively enabling absorption of at least the liquid portion of the sample (if the sample inherently includes a liquid portion, and/or the aforementioned combined liquid sample (not shown) which is to be specified in greater detail hereinbelow). The absorbent layer is in intimate contacting relation with the protein layer. The test system may also include, without limitation, an optional housing which may or may not be present as part of the test system. The housing (if present) may substantially encapsulate the passage layer, the protein layer, and the absorbent layer. The housing (if present) may preferably, but need not necessarily, have a substantially non-porous structure and/or be in intimate contacting relation with the absorbent layer and/or with said passage layer. The housing (if present) may or may not include an upper portion which may preferably, but need not necessarily, define at least one housing aperture. The at least one housing aperture (if present) may preferably, but need not necessarily, be substantially aligned with the at least one aperture of the passage layer. Preferably, in a positive result configuration, the marker proteins may be bound to the combinable proteins and immobilized relative to the protein layer. In a negative result configuration, at least a portion of the liquid portion (if present) of the sample (and/or at least a portion of the aforementioned combined liquid sample (not shown) which is to be specified in greater detail hereinbelow) may preferably, but need not necessarily pass substantially through the protein layer.

With further reference to FIGS. 8 through 16 of the drawings, and in addition to, and/or in contradistinction from, any other portions and/or embodiments of the test system which are described elsewhere herein, according to one aspect of the invention, the test system may include a wash structure 700, 702 (e.g., a wash tablet 700, and/or a mixing bowl 702) that is pre-formed in and/or secured to, and/or selectively formable in and/or securable to, at least one upper outer surface 704 of the test kit. The upper outer surface 704 may be a passage layer surface and/or a housing surface (if present). Preferably, the wash structure 700, 702 is substantially adjacent to and/or aligned with a test aperture 706 of the system. The test aperture 706 is defined by the at least one aperture in the passage layer and/or by the housing aperture (if present). According to this aspect of the invention, in the operative configuration, the sample may preferably, but need not necessarily, be combined with a suitable wash solution (not shown) on, and/or in, the wash structure 700, 702 to form a combined liquid sample (not shown). The combined liquid sample (not shown) may preferably, but need not necessarily, be then caused to flow, possibly under the influence of gravity, from the wash structure 700, 702 to the test aperture 706. In this manner, the combined liquid sample (not shown) may preferably, but need not necessarily, be introduced onto the protein layer through the at least one aperture of the passage layer.

With more specific reference to FIGS. 8 through 13 of the drawings, and in addition to, and/or in contradistinction from, any other portions and/or embodiments of the test system which are described elsewhere herein, according to one aspect of the invention, the test system may include a mixing bowl 702 that is pre-formed, and/or selectively formable, in at least one upper outer surface 704 of the test kit. The bowl 702 is formed, and/or formable, substantially adjacent to the test aperture 706. In the operative configuration, the sample may preferably, but need not necessarily, be combined with a suitable wash solution (not shown) in the mixing bowl 702 to form a combined liquid sample (not shown). The combined liquid sample (not shown) may preferably, but need not necessarily, be then caused to flow, by tipping and/or inclining the test kit (in the direction generally indicated by arrows "Z") and/or under the influence of gravity, from the bowl 702 to the test aperture 706. In this manner, the combined liquid sample (not shown) may preferably, but need not necessarily be, introduced onto the protein layer through the at least one aperture of the passage layer.

According to one aspect of a preferred embodiment of the invention, the upper outer surface 704 of the test kit may preferably, but need not necessarily, be provided with at least one pre-formed, and/or selectively formable, channel 708 that runs between the mixing bowl 702 and the test aperture 706. The combined liquid sample (not shown) may preferably, but need not necessarily, flow from the bowl 702 to the test aperture 706 substantially within the channel 708.

Figure 12:
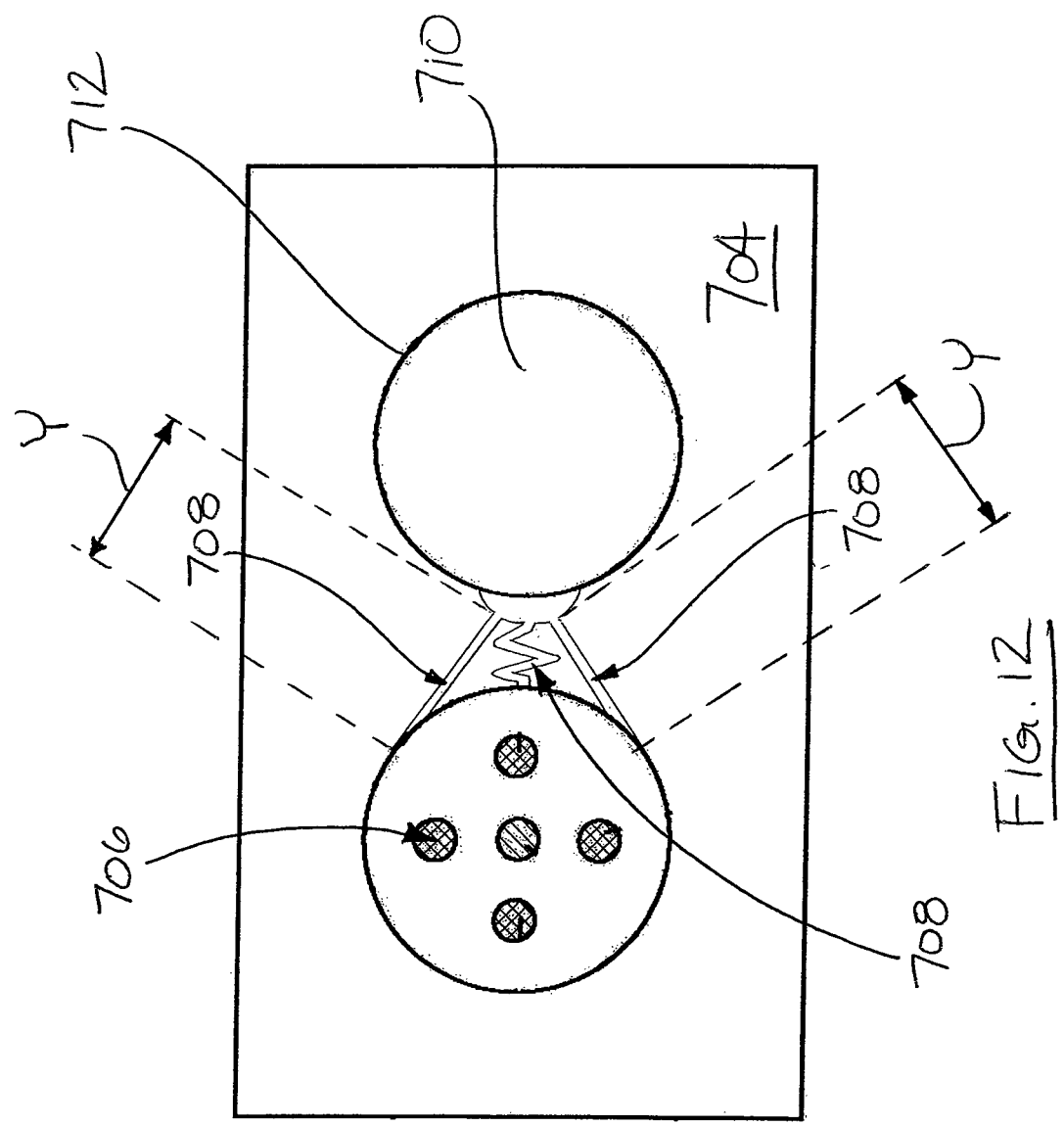
FIG. 12 is a top plan view of a further preferred embodiment of the test system similar to that shown in FIG. 11, but shown with three channels of substantially similar lengths.

According to another aspect of a preferred embodiment of the invention (and as best seen in FIG. 12), the at least one channel 708 may preferably, but need not necessarily, comprise a plurality of channels 708 running between the mixing bowl 702 and the test aperture 706.

According to another aspect of a preferred embodiment of the invention, and as best seen in FIG. 12, the combined liquid sample (not shown) in each one of the plurality of channels 708 may preferably, but need not necessarily, traverse substantially the same distance (as indicated generally by the dimension lines "Y") between the mixing bowl 702 and the test aperture 706 as the combined liquid sample (not shown) in each other one of the plurality of channels 708.

Figure 8:
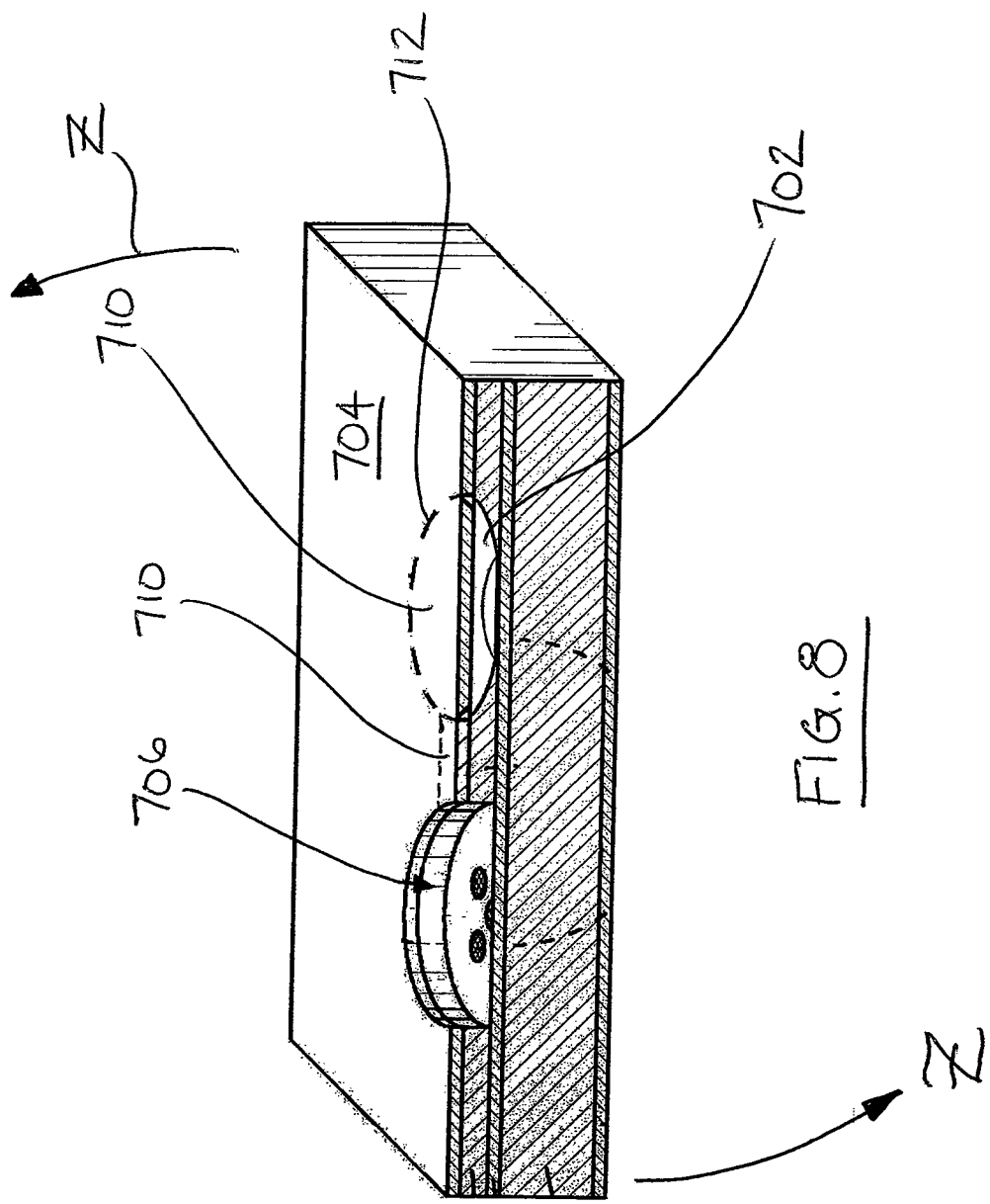
FIG. 8 is a top front left cross-sectional perspective view of another preferred embodiment of a test system according to the invention that includes frangible areas over a mixing bowl and a channel.
Figure 9:
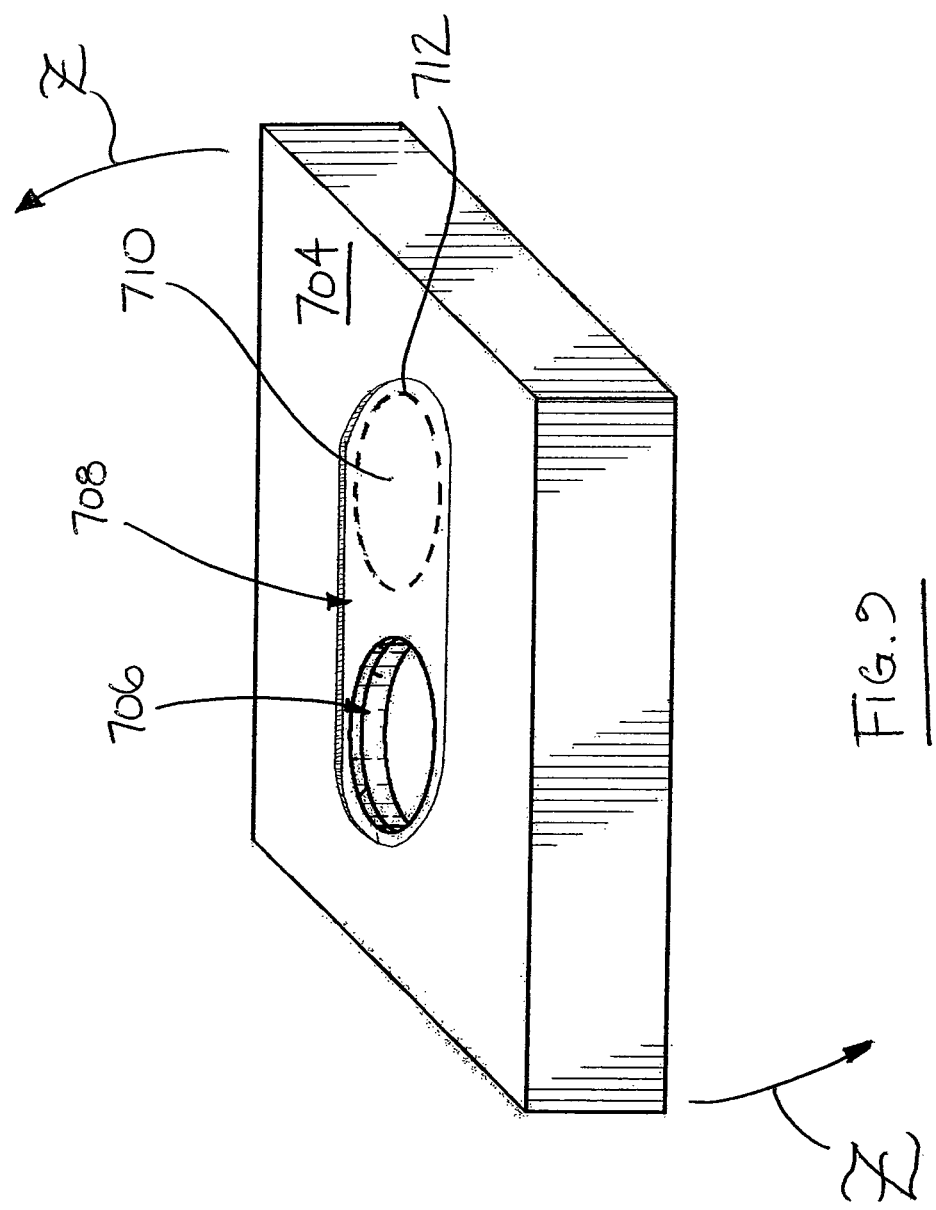
FIG. 9 is a top front left perspective view of another preferred embodiment of a test system according to the invention that includes a channel and a frangible area over a mixing bowl.
Figure 10:
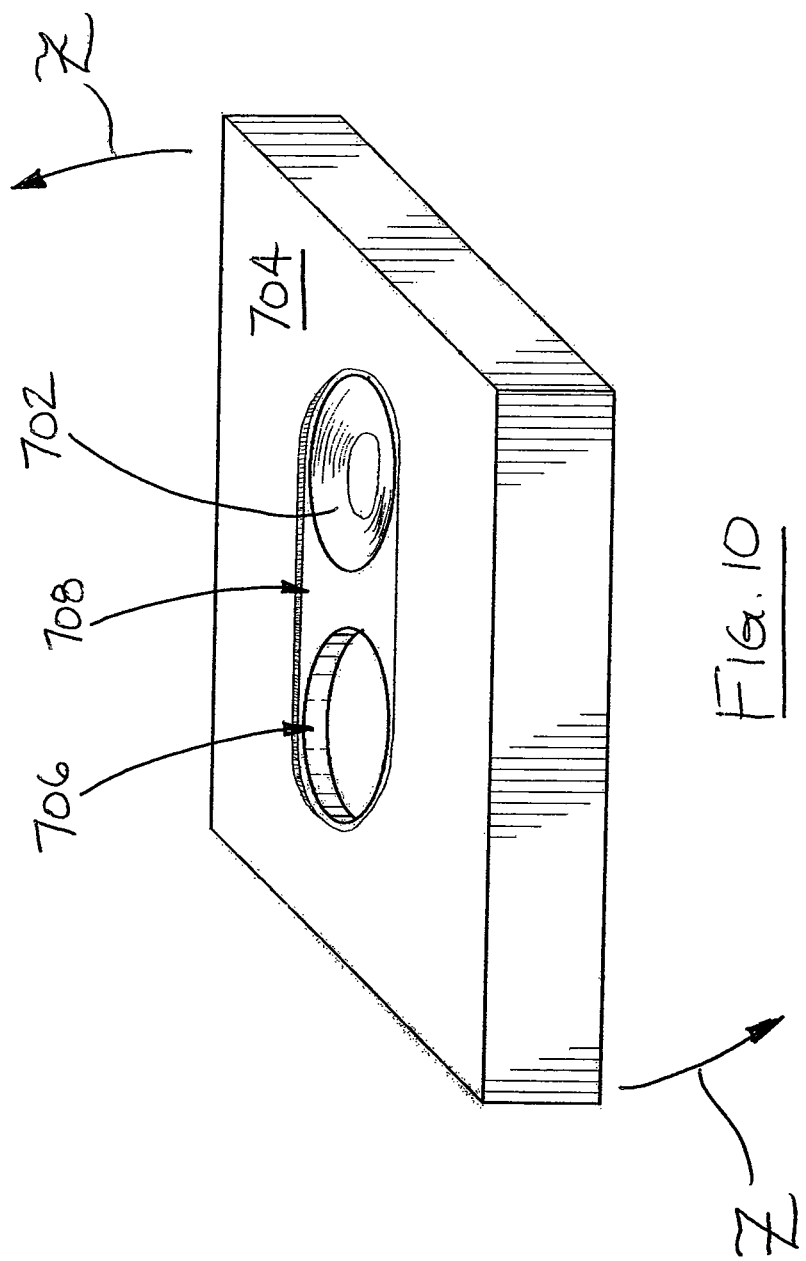
FIG. 10 is a view of a test system similar to that shown in FIG. 9, but shown without any frangible area and with one less housing layer.
Figure 11:
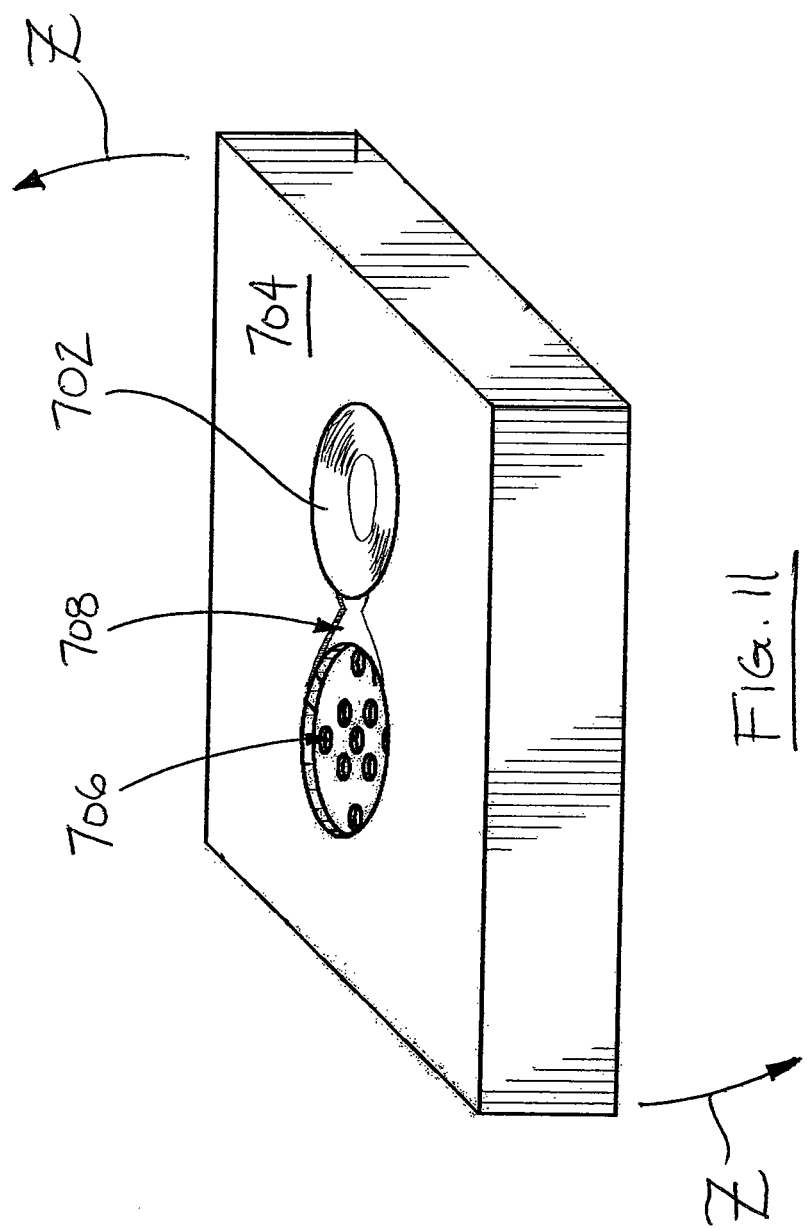
FIG. 11 is a view of a test system similar to that shown in FIG. 10, but shown with a different shaped channel and a plurality of passage layer apertures.

According to one aspect of another preferred embodiment of the invention (and as best seen in FIGS. 8, 9 and 12), one or more of the mixing bowl 702 and the channel(s) 708, if present, may preferably, but need not necessarily, be selectively formable by depressing (and/or removing) at least one frangible area 710 that is preferably, but not necessarily, provided on the upper outer surface 704 of the test kit.

According to one aspect of another preferred embodiment of the invention, and as best seen in FIGS. 8, 9 and 12, the upper outer surface 704 of the test kit may preferably, but need not necessarily, be marked with at least one local indicium 712 (such as, for example and without limitation, a dotted and/or solid outline)—preferably, but not necessarily, to indicate the location of the frangible area 710.

Figure 13:
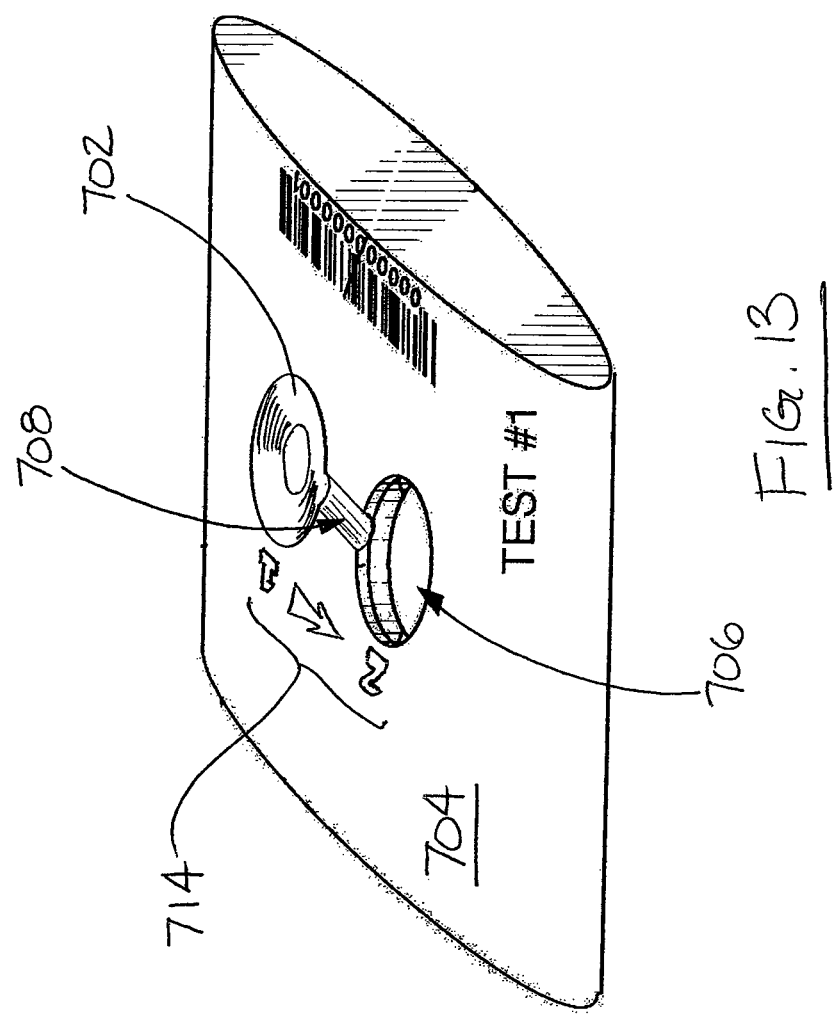
FIG. 13 is a top front left perspective view of still another embodiment of the test system according to the invention, shown with a different shaped channel and with instructional indicia.

According to one aspect of another preferred embodiment of the invention, and as best seen in FIG. 13, the upper outer surface 704 of the test kit may preferably, but need not necessarily, be marked with at least one instructional indicium 714 (such as, for example and without limitation, (i) the letters "A" and "B" positioned adjacent to the mixing bowl 702 and test aperture 706, respectively; (ii) the numbers "1" and "2" positioned adjacent to the mixing bowl 702 and test aperture 706, respectively; and/or (iii) an arrow pointing from the mixing bowl 702 to the test aperture 706)—preferably, but not necessarily, to suggest one preferable use of the mixing bowl 702, in order, before use of the test aperture 706.

According to one aspect of another preferred embodiment of the invention, the mixing bowl 702 may preferably, but need not necessarily, be sized to accommodate a volume of the combined liquid sample (not shown) which is substantially greater than, or substantially equal to, the volume of the combined liquid sample (not shown) which may preferably be accommodated within the test aperture 706.

Figure 14:
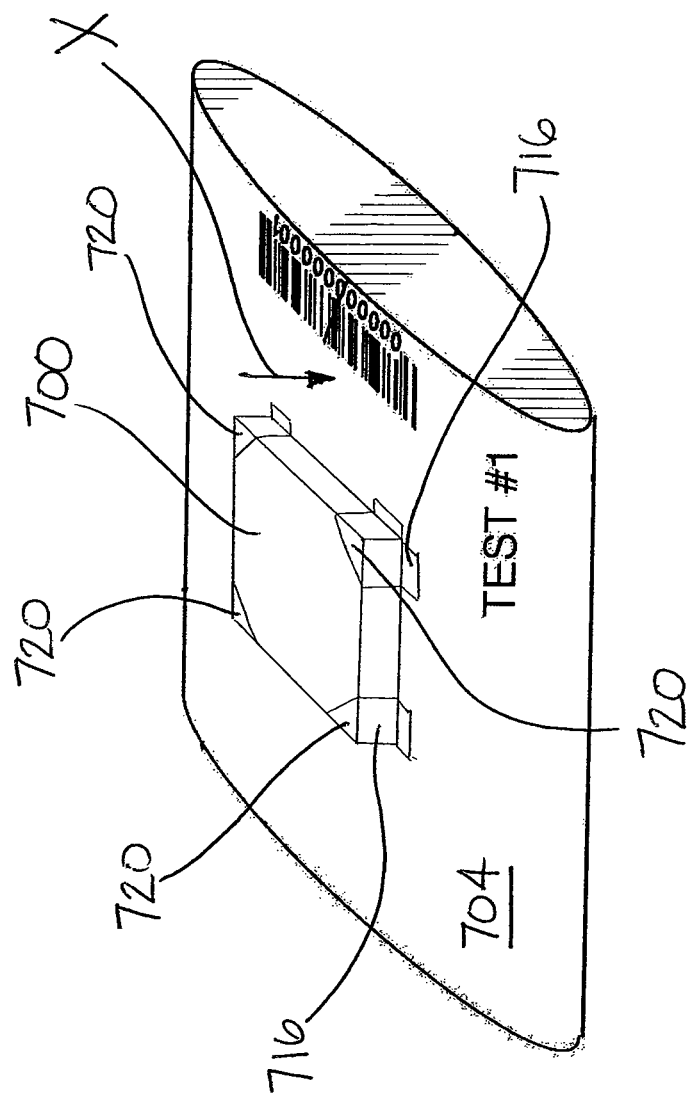
FIG. 14 is a top front left perspective view similar to FIG. 13 of a further preferred embodiment of the test system, shown with a wash tablet and tape securing means.

Now, with more specific reference to FIGS. 14 through 16 of the drawings, and in addition to, and/or in contradistinction from, any other portions and/or embodiments of the test system which are described elsewhere herein, according to one aspect of the invention, the test system may include a wash tablet 700 that is secured, and/or selectively securable, to at least one upper outer surface 704 of the test kit. The wash tablet 700 may preferably, but need not necessarily, be secured and/or securable, in substantially overlying relation, above the test aperture 706. In the operative configuration, the sample may preferably, but need not necessarily, be combined with a suitable wash solution (not shown) on and/or in the wash tablet 700 to form the combined liquid sample (not shown). The combined liquid sample (not shown) may preferably, but need not necessarily, then be caused to flow, by a wicking effect (in the direction generally indicated by arrow "X" in FIG. 14) and/or under the influence of gravity, from the wash tablet 700 to the test aperture 706. In this manner, the combined liquid sample (not shown) may preferably, but need not necessarily, be introduced onto the protein layer through the at least one aperture of the passage layer.

According to one aspect of a preferred embodiment of the invention, and in order to facilitate the wicking effect "X" (which is best seen in FIG. 14), the tablet 700 may preferably, but need not necessarily, be in intimate contacting relation (not shown) with the protein layer of the test kit.

According to one aspect of a preferred embodiment of the invention, the wash solution (not shown) may preferably, but need not necessarily, be introduced into the tablet 700 before the sample.

According to one aspect of another preferred embodiment of the invention, the tablet 700 may preferably, but need not necessarily, be saturated with the wash solution (not shown) before the sample is introduced into the tablet 700.

According to one aspect of another preferred embodiment of the invention, the wash tablet 700 may preferably, but need not necessarily, be constructed—whether in part or entirely—from a material that is selected from the group which includes, without limitation, glass fiber materials (such as, for example and without limitation, spun fiberglass), other synthetic fiber materials (such as, for example and without limitation, nylon), paper materials (such as, for example and without limitation, cellular acetate, loose cardboard materials, paper towels), and/or sponge materials (preferably, but not necessarily, of a specified minimum porosity).

According to one aspect of another preferred embodiment of the invention, the wash tablet 700 may preferably, but need not necessarily, be constructed—whether in part or entirely—from a first material that is operatively impregnated with a second material (such as, for example and without limitation, a lectin) that binds to cellular, lipid and/or particulate portions of the sample. The first and second materials may preferably, but need not necessarily, also allow substantially unimpeded passage of the analytes therethrough.

According to one aspect of another preferred embodiment of the invention, and as best seen in FIGS. 14 and 15, the wash tablet 700 may preferably, but need not necessarily, be secured and/or selectively securable to the upper outer surface 704 of the test kit by securing means 716, 718. The securing means 716, 718 may, for example and without limitation, be a tape 716 (as best seen in FIG. 14) and/or an adhesive 718 (as best seen in FIG. 15).

According to another aspect of a preferred embodiment of the invention, and as best seen in FIG. 14, the securing means 716, 718 may preferably, but need not necessarily, be applied substantially adjacent to corners 720 and/or edges of the wash tablet 700.

According to another aspect of another embodiment of the invention, and as best seen in FIG. 14. the tape 716 (e.g., scotch tape 716) may, but need not necessarily, be applied over top of the wash tablet 700.

According to one aspect of another preferred embodiment of the invention, after the combined liquid sample (not shown) is introduced onto the protein layer, the wash tablet 700 may preferably, but need not necessarily, be peeled back—in the general direction of arrow "W" in FIG. 15—(and/or otherwise removed) from the test aperture 706 (and/or otherwise rendered observably non-obstructing) to reveal the positive result configuration and/or the negative result configuration.

According to one aspect of another preferred embodiment of the invention, one or more of the passage layer, the protein layer, the absorbent layer, the housing (if present), the wash structure 700, 702 (if present), and/or the wash tablet 700 (if present) may preferably, but need not necessarily, be constructed of one or more combustible materials. One or more of such combustible materials may preferably, but need not necessarily, produce non-toxic by-products upon incineration.

According to one aspect of another preferred embodiment of the invention, one or more of the passage layer, the protein layer, the absorbent layer, the housing (if present), the wash structure 700, 702 (if present), and/or the wash tablet 700 (if present) may preferably, but need not necessarily, be constructed of a densely packed paper material.

As aforesaid, the various preferred embodiments of the test system 70 that are shown in the drawings are each preferably, but not necessarily, adapted to test for the presence of marker proteins in a liquid sample analyte (not shown). The liquid sample analyte is the sample that is intended to be tested by the system 70, which sample may or may not contain the sought-after marker proteins. That is, the liquid sample analyte is the substance or constituent being tested or undergoing analysis, and includes, for example, liquid sample matrices, serums, plasmas, perspiration, urine samples, and/or other aqueous extracts that contain body substances in which tissue cells are embedded and/or suspended. Other analytes that may preferably, but not necessarily, be capable of testing using the system 70 might include environmental samples, such as, for example, well water samples. Accordingly, the test system 70 may preferably be adapted to test for the presence of marker proteins from a broad class, including those of a biological, agricultural, veterinary, and/or environmental origin.

By way of example, in an agricultural application, the system 70 may be used, in conjunction with aqueous plant or leaf extracts, to detect for the presence of various diseases in banana plants, such as, for example, the banana bract mosaic virus (a common banana plant disease in areas such as India, the Philippines and Sri Lanka), and/or the abaca mosaic virus (a common banana plant disease in the Philippines).

Similarly, in a veterinary setting, the system 70 may be used to detect for the presence of various diseases in animals and/or household pets, such as dogs or cats. For example, the system 70 might be used to detect for the presence of heartworm disease and/or other diseases, such as, for example, leishmaniasis, parvo viral infections, and/or lyme disease.

By way of yet another example, the system 70 may preferably, but not necessarily, also be used to detect for the presence of various environmental pollutants, such as, for example, gasoline additives like methyl tertiary butyl ether. In the case of such gasoline additives, and while they may typically be used to benefit air quality by reducing automobile emissions, they may also problematically find their way to groundwater supplies that may ultimately be destined for human consumption.

By way of yet a further example, the test system 70 may also be used to detect for the presence of various diseases common to humans that may be caused by any number of pathogens. For example, the test system 70 of the present invention may be capable of use to simultaneously detect for the presence of causative agents associated with a number of diseases, such as cardiovascular diseases. In the case of cardiovascular diseases, the causative agents may include a wide number of differing pathogens, such as, for example, agents of viral, fungal and/or bacterial origin. In such a test, the system 70 might also be used to test for the presence of antibodies to healthy cell markers, such as, for example, the protein myosin which is found in heart muscles, and/or to any of the causative agents listed hereinabove.

The particular applications of the test system 70 which are discussed herein are merely intended to serve as examples of the testing capabilities of the invention, and are not intended to limit the potential applications of the test system 70 and its varied uses in conjunction with various liquid sample analytes.

Operatively, the protein layer 14 of the test device 70 will preferably have combinable proteins (not shown) bound to and/or substantially immobilized thereon. Within the scope of the invention, the combinable proteins may be stuck onto a surface of the protein layer 14 and/or they might be substantially embedded therein. Indeed, a wide variety of different manners of binding and/or affixation of the combinable proteins to the protein layer 14 will preferably fall within the scope of the invention.

The combinable proteins that are operatively bound to the protein layer 14 of the test system 70 may preferably be specifically selected to correspond with the test to be conducted and/or so as to ensure binding with the sought-after marker proteins that may be present in the particular liquid sample analyte that is to be tested. For example, and without limitation, if the test system 70 is intended to test for the presence of HIV 1, then combinable proteins that are particularly well suited to bind with HIV 1 and/or its marker proteins might be substantially immobilized on the protein layer 14. Similarly, if the test system 70 is to be used to test for Hepatitis C, then combinable proteins that are particularly well suited to bind with Hepatitis C and/or its marker proteins might be substantially immobilized on the protein layer 14.

As stated above, the test system 70 may preferably, but not necessarily, be used to simultaneously detect for the presence of causative agents for a wide number of diseases, including, for example, agents of viral, fungal and/or bacterial origin, with corresponding combinable proteins immobilized on the protein layer 14 in such instances. That is the combinable proteins may comprise proteins which are adapted to be bound to fungal marker proteins, viral marker proteins, bacterial marker proteins, and/or vector-induced marker proteins, as may be present in the tested liquid sample analyte.

It may be appreciated that the protein layer 14 is a "reaction zone" of the test system 70. In an operative configuration according to the invention, the combinable proteins will preferably be substantially immobilized on the protein layer 14, and more preferably, on the active surface area 30 and visible portion 31 of the protein layer 14. According to the invention, the nitrocellulose or other protein layer 14 of the test system 70 may preferably be provided to the end user (not shown) with the combinable proteins already substantially immobilized thereon. Alternately, the combinable proteins may also preferably be immobilized on the protein layer 14 at, or near, the time of testing. In either event, and as aforesaid, the combinable proteins will preferably be those to which the sought-after marker proteins, if present in the tested subject liquid sample analyte, will affix such as by sticking or binding.

It is contemplated, though not essential to the working of the system 70, that the combinable proteins may preferably be immobilized directly onto the protein layer 14 in the general vicinity of the active surface area 30, and more preferably in the visible portion 31 of the active surface area 30. The combinable proteins may be immobilized in the visible portion 31 of the active surface area 30 in any desired pattern, shape or design, even after the test system 70 has been fully assembled. For example, and without limitation, after assembly of the test system 70, HIV 1 combinable proteins might preferably be immobilized on the active surface area 30 in the visually discernable form of a numeral "1" (not shown), and likewise, Hepatitis C combinable proteins might preferably be immobilized thereon in the form of the letter "C". Of course, any such other format might be used to suit the user and/or manufacturer of the test system 70.

According to the invention, combinable proteins may be substantially immobilized on the protein layer 14 by applying and/or depositing a combinable protein solution (not shown) onto the active surface area 30 of the protein layer 14, such as, for example, by ink jet spraying, by physically using a pipette, and/or by touching the combinable protein solution onto the designated area of the nitrocellulose membrane or other protein layer 14, such that the combinable proteins might then be absorbed onto the protein layer 14 by suction and/or capillary action.

It should therefore be appreciated that, prior to testing, when the test system 70 is assembled in the operative configuration, combinable proteins for the detection of a plurality of different marker proteins in the liquid sample analyte may preferably be selected and/or immobilized, in any useful pattern on the protein layer 14, substantially in the region of the active surface area 30.

With the combinable proteins substantially immobilized to the active surface area 30 of the protein layer 14, marker proteins (not shown) in the liquid sample analyte may be permitted, in some of the contemplated uses discussed hereinbelow, to become substantially immobilized relative to the protein layer 14.

Figure 4A:
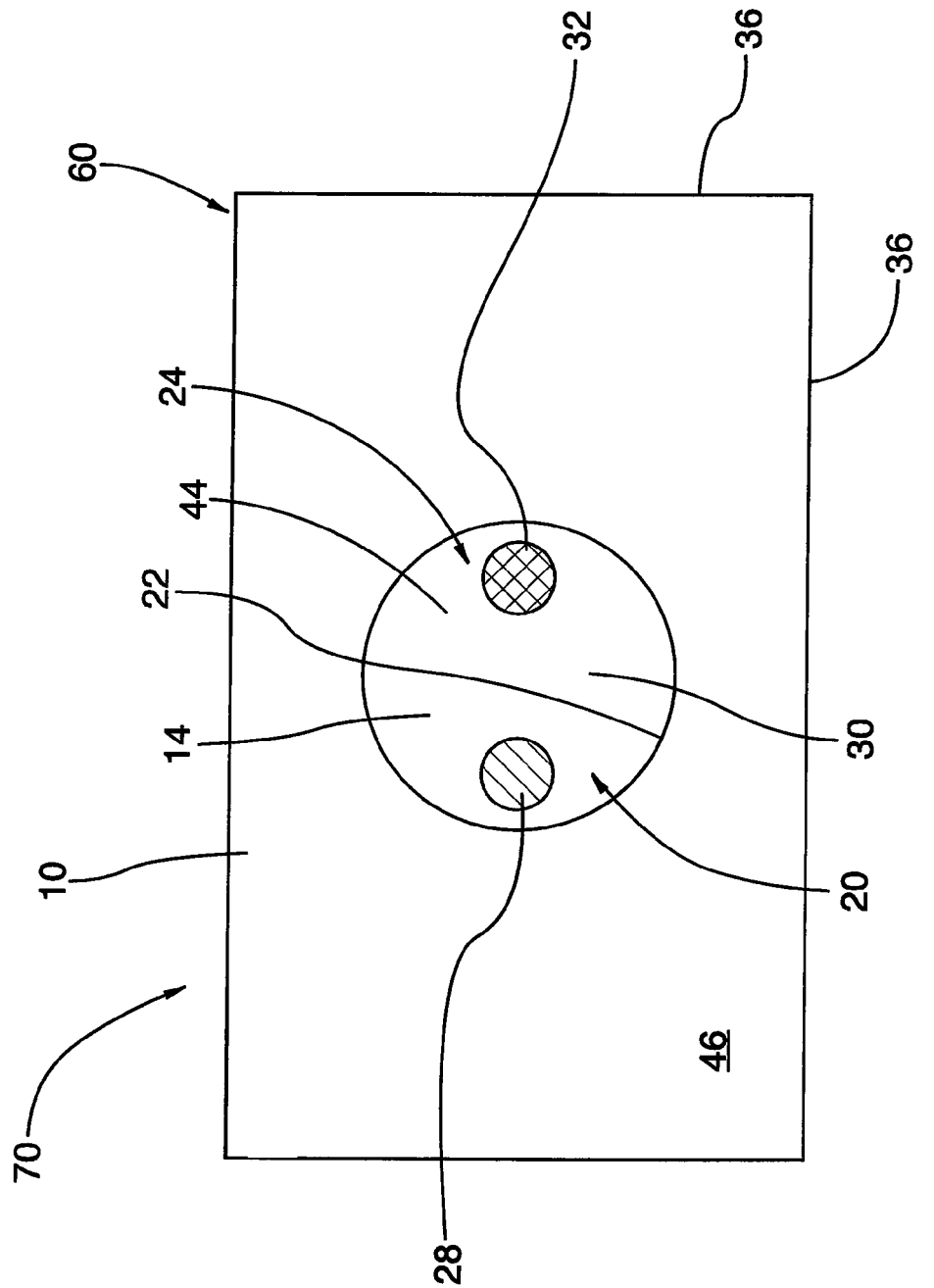
FIG. 4A is a top plan view of a further preferred embodiment of the test system according to the invention which is similar to that shown in FIG. 2A.
Figure 4B:
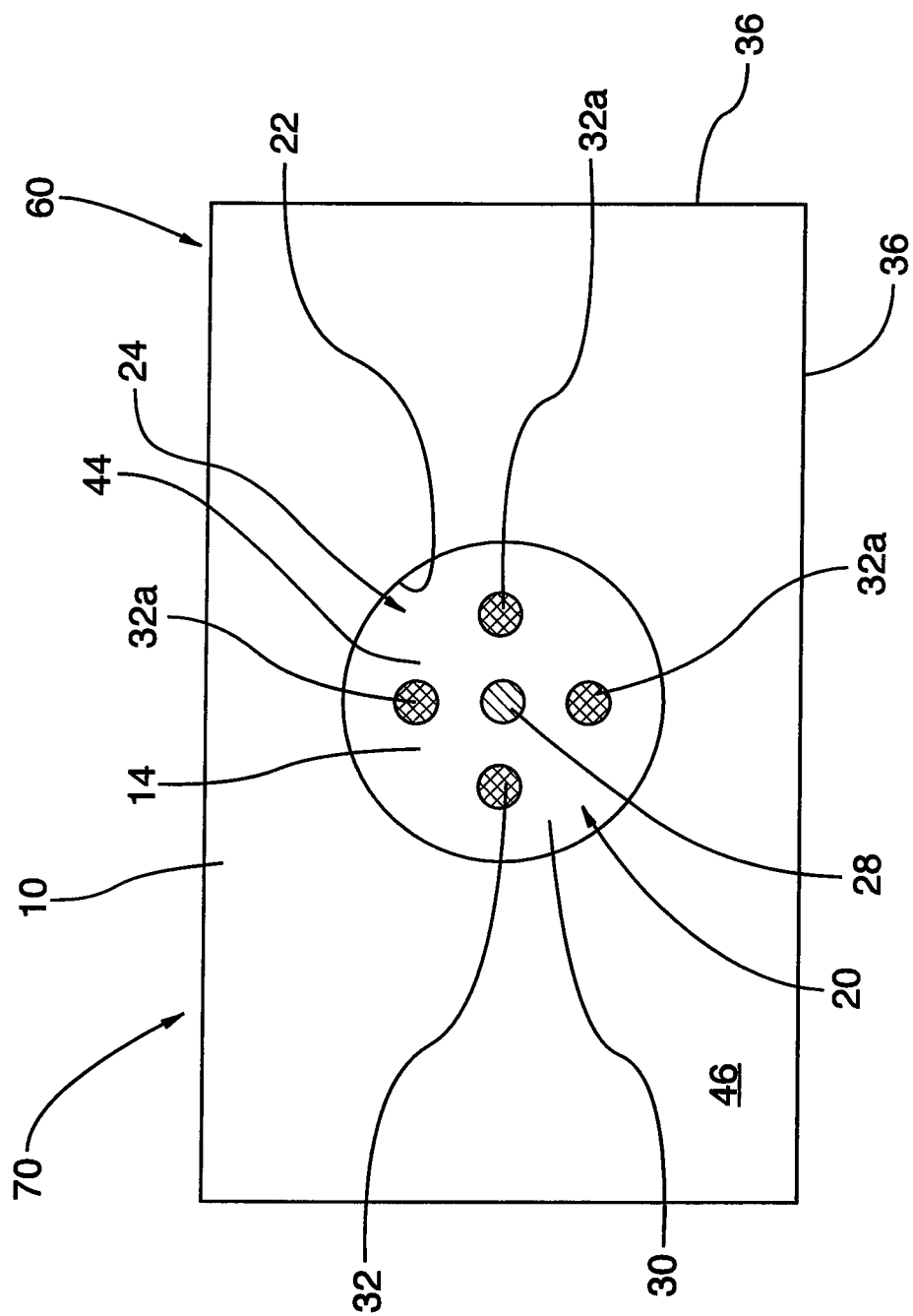
FIG. 4B is a top plan view of the test system of FIG. 2A.

As best seen in FIGS. 4A and 4B, the active surface area 30 is preferably viewable, by the user, through the housing aperture 20 and the aperture 24 in the passage layer. In the embodiment shown in FIGS. 4A and 4B, the active surface area 30 includes a first test surface area 32 and a procedural control surface area 28. In the operative configuration, the combinable proteins immobilized on the protein layer 14 are substantially immobilized on the first test surface area 32. The procedural control surface area 28 is adapted to display a control reading both in a positive result configuration (as shown in FIGS. 4A and 4B) and in a negative result configuration (not shown) of the test system 70, so as to preferably confirm that it has been used, handled and/or stored properly.

More specifically, and as best seen in FIGS. 4A and 4B, if the test system 70 has been used, handled and stored properly, a control reading may preferably be generated in and displayed from the procedural control surface area 28. The control reading may preferably, but not necessarily, take the form of a color or other indication that may correspond to a pattern of the combinable proteins that are operatively immobilized on the active surface area 30 of the protein layer 14, as discussed above.

The absence of a control reading in the procedural control surface area 28 might preferably indicate that any test performed using the system 70 may be invalid. It should be appreciated that, while the procedural control surface area 28 need not, strictly speaking, be present in the test system 70 according to the invention, it is preferably present.

If a single type of qualitative marker protein test is to be performed using the system 70, the procedural control surface area 28 may preferably, but not necessarily, be arranged in relation to the first test surface area 32 in the manner depicted in FIG. 4A.

Alternately, if a quantitative marker protein test is to be performed using the system 70, the procedural control surface area 28 may preferably, but not necessarily, be located in a substantially central location of the active surface area 30, as shown in FIG. 4B. In FIG. 4B, the active surface area 30 may preferably further comprise a supplemental first test surface area 32a. The same combinable proteins are preferably operatively immobilized on both the first test surface area 32 and the supplemental first test surface area 32a, albeit in preferably, though not necessarily, different concentrations. For example, a substantially higher concentration of combinable proteins may be substantially immobilized on the supplemental first test area 32a relative to a concentration of the combinable proteins on the first test surface area 32.

Likewise, and as best seen in FIG. 4C, if the user wishes to test for the presence of multiple marker proteins at substantially the same time using a single system 70, the procedural control surface area 28 may preferably, but not necessarily, be located in a substantially central location of the active surface area 30. As shown in FIG. 4C, the active surface area 30 may additionally include a second test surface area 33, with a second set of different combinable proteins (not shown) operatively immobilized thereon. The second set of combinable proteins may preferably be selected and/or adapted to detect for the presence of different marker proteins than those of the (first set of) combinable proteins. Likewise, the second set of combinable proteins may immobilized in any useful pattern on the protein layer 14.

In addition to the first test surface area 32, the supplemental first test surface area 32a, and the second test surface area 33, and as shown in FIG. 4C, the active surface area 30 may also include a supplemental second test surface 33a. The same combinable proteins are preferably operatively immobilized on both the second test surface area 33 and the supplemental second test surface area 33a, albeit in preferably, though not necessarily, different concentrations. For example, a substantially higher concentration of combinable proteins may be substantially immobilized on the supplemental second test area 33a relative to a concentration of the combinable proteins on the second test surface area 33.

As best seen in FIG. 4C, the first test surface area 32 and the supplemental first test surface area 32a may preferably, but not necessarily, together notionally define a substantially planar first test ring 40. Each of the first test surface area 32 and the supplemental first test surface area 32a are preferably, but not necessarily, notionally situated therewithin. In such a configuration, the procedural control surface area 28 may preferably, but not necessarily, be substantially circumscribed within the first test ring 40.

The second test surface area 33 and the supplemental second test surface area 33a may also preferably, but not necessarily, together notionally define a substantially planar second test ring 42. Each of the second test surface area 33 and the supplemental second test surface area 33a are preferably, but not necessarily, notionally situated therewithin. In such embodiments, and as best seen in FIG. 4C, the second test ring 42 may preferably, but not necessarily, substantially circumscribe the first test ring 40.

Alternatively, the first test surface area 32, the supplemental first test surface area 32a, the second test surface area 33, the supplemental second test surface area 33a, and the procedural control surface area 28 may together notionally define various configurations, such as, for example, various other concentric and/or non-concentric geometric shapes. Of course, other geometric shapes may be formed that may, for example, comprise differing a multiple number of concentric shapes.

In another contemplated embodiment of the invention, the first and/or the second test surface area 32, 33 may consist of mimicry surface areas. More specifically, the combinable proteins substantially immobilized on the first and/or second test surface areas 32, 33 may be native proteins that are biosynthesizable by substantially healthy cells in the liquid sample analyte and/or a species furnishing same.

Figure 4D:
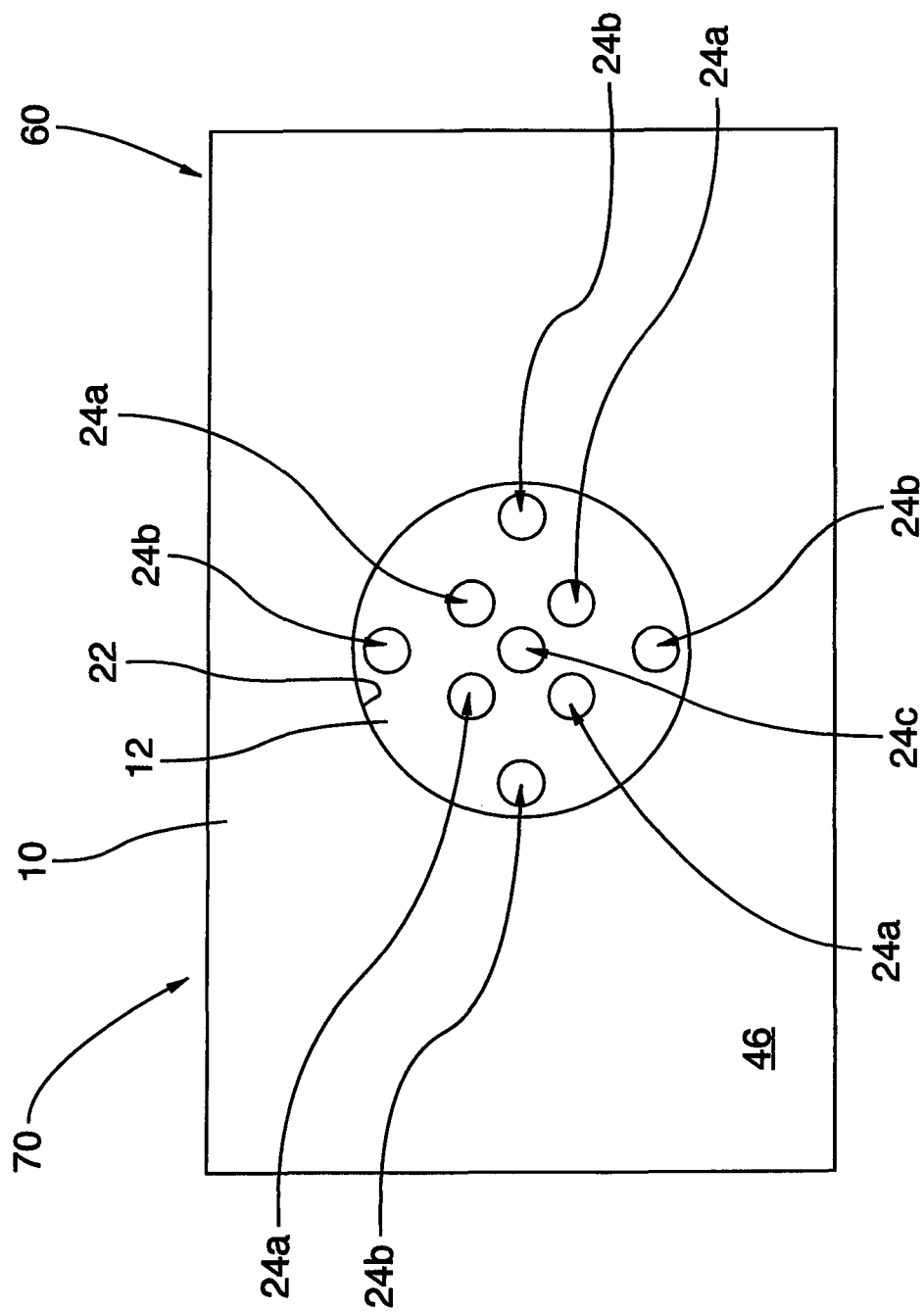
FIG. 4D is a top plan view of the test system of FIG. 2D, showing the upper housing portion and the passage layer.

The embodiment of the test system 70 that is shown in FIGS. 4D and 4E is perhaps deserving of some additional explanation. In this embodiment, and as aforesaid (i.e., corresponding generally to the discussion of FIGS. 2D through 2F hereinabove), the passage layer 12 is formed with first and second apertures 24a, 24b, and a control aperture 24c therethrough. As may be best appreciated from a consideration of FIGS. 2E and 4E, the first apertures 24a are substantially aligned "A" with the first test ring 40, the second apertures 24b are substantially aligned with the second test ring 42, and the control aperture 24c is substantially aligned with the procedural control surface area 28 on the protein layer 14.

The use of the test system 70 will now be described with reference to the various embodiments which are depicted in the drawings. It should, however, be appreciated, that the following discussion of use may also preferably, but not necessarily, apply generally to other embodiments which are not illustrated, but which may fall within the scope of the invention.

In a typical test, and prior to applying and/or testing the liquid sample analyte, a first drop of wash buffer is preferably added to the test system 70 through the housing aperture 20 of the upper housing portion 10, to wet the visible portion 31 of the active surface area 30 on the protein layer 14, and is allowed to adsorb. The wash buffer will preferably, but not necessarily, act as a blocker for any areas on the active surface area 30 where no combinable proteins have been immobilized, so as to provide an inactive protein wash bound area 44 (as seen in, for example, FIGS. 4A and 4B), thus preferably preventing the indiscriminate affixation of marker and/or other proteins from the liquid sample analyte thereon.

The liquid sample analyte may preferably then be introduced, using a pipette or the like, through the housing aperture 20 of the test system 70. The housing aperture 20 is in operative fluid communication with the passage layer aperture 24, such that the liquid sample analyte may preferably be deposited onto the active surface area 30 of protein layer 14 through the at least one aperture 24 of the passage layer 12. The liquid sample analyte may be operatively introduced through the housing aperture 20 in a quantity that is preferably, though not necessarily, sufficient to cover the visible portion 31.

As aforesaid, the test system 70 of the present invention tests for the presence of marker proteins in the liquid sample analyte. In a positive result configuration, and as best shown in FIGS. 4A through 4E, use of the test system 70 will preferably reveal that the sought-after marker proteins are actually present in the liquid sample analyte. In the positive result configuration, one or more marker proteins from the liquid sample analyte will preferably be bound to the combinable proteins and substantially immobilized relative to active surface area 30 of the protein layer 14.

In the event that the analyte contains both first and second sought-after marker proteins, and in the further event that the active surface area 30 includes both first and second test surface areas 32, 33, the first and second test surface areas 32, 33 may preferably have the first and second marker proteins respectively bound thereto in the positive result configuration.

In the event that, as aforesaid, the combinable proteins comprise native proteins substantially immobilized on the mimicry surface area, in the positive result configuration, the marker proteins may preferably be bound to the native proteins and substantially immobilized relative to the protein layer.

Conversely, in a negative result configuration, the use of the test system 70 will preferably not reveal the presence of any of the marker proteins in the liquid sample analyte. In the negative result configuration (not shown), at least a portion and preferably most and/or substantially all of the liquid sample analyte will pass substantially through the protein layer 14, without affixing to any of the combinable proteins immobilized thereon.

In any event, and whether due in part to gravity or under an influence of another force (such as, for example, inertial forces which may be created in a centrifuge), a portion of the liquid sample analyte may preferably traverse substantially vertically through the test system 70, and/or across the protein layer 14, away from its point of entry.

Preferably, a sufficient quantity of the liquid sample analyte will be introduced onto the protein layer 14 so as to ensure that any sought-after marker proteins which may be contained therein become substantially immobilized relative to the protein layer 14 (in a positive result configuration) or not (in a negative result configuration).

The aforesaid substantially porous structure of the protein layer 14 preferably enables a portion of the liquid sample analyte to pass therethrough. In the event of liquid sample analytes that contain particulate matter (such as whole blood), that are lipaemic, and/or that may require further clarification or amplification may not filter through pore sizes smaller than about 5 to 6 microns in the protein layer 14, such liquid sample analytes may preferably, but not necessarily, be clarified and/or broken down prior to testing. Liquid sample analytes that may be tested without further clarification and/or amplification may preferably include, for example, serum, plasma, urine, perspiration and/or exudates. Other aqueous extracts that may preferably be clarified by filtration and/or centrifugation may also form a part of the analyte to be tested using with test system 70.

Thereafter, a drop or other necessary quantity of a reagent may preferably then be added, in a preferred quantity that covers the visible portion 31 of the active surface area 30. The reagent is particularly selected and/or adapted to operatively bind to any marker proteins that may have been substantially immobilized relative to the protein layer 14 in the positive result configuration.

In one embodiment of the invention, the reagent (not shown) may preferably comprise a visually tagging substance that, when specifically bound to any marker proteins affixed to the combinable protein that are immobilized on the protein layer 14, provides colored indicia indicating and/or confirming that the test system 70 is in the positive result configuration. The visually tagging substance (not shown) may comprise any one or more of a variety of substances, such as, for example, a radioactive isotope substance, a fluorescent substance, a UV absorbing substance, and/or a colored substance. The colored visually tagging substances may consist of a colloidal carbon conjugate substance, a colloidal gold conjugate substance, a dyed latex bead substance, and/or the like.

Preferably, for analytes in nanogram to femtogram quantities, amplifications by enzyme conjugates may be necessary. Situations where amplifications by enzyme conjugates may be preferable might include, for example, IgE detection in allergy diagnosis, and/or detection for drug abuse, industrial and environmental pollutants, diseases in plants, hormones, cancer markers, arthritis markers, and/or the like.

Where these and/or other quantities of analytes are to be used, the aforesaid reagent may comprise a protein enzyme conjugate substance (not shown). As with the other reagents used according to the invention, the protein enzyme conjugate substance is particularly selected and/or adapted to operatively bind to any marker proteins that may have been substantially immobilized relative to the protein layer 14 in the positive result configuration.

At that point, an additional drop of the same or a different wash buffer may then preferably be added to the active surface area 30 to preferably, but not necessarily, wash away any unbound material. At this point, the wash buffer may be allowed to adsorb into the protein layer 14.

In situations where the aforesaid reagent comprises a protein enzyme conjugate substance, an enzyme substrate substance (not shown) may then be preferably added. Thereafter, the user will wait for a suitable period of time to elapse, possibly in the order of approximately 10 to 60 seconds, during which period the enzyme substrate substance will be afforded an opportunity to operatively bind to the protein enzyme conjugate substance in the positive result configuration. The protein enzyme conjugate substance and the enzyme substrate substance are together selected and/or adapted to operatively display coloured indicia indicating and/or confirming that the test system 70 is in the positive result configuration. In this embodiment of the test system 70, an additional drop of wash buffer may preferably then be added through housing aperture 20, and allowed to traverse substantially vertically away from its point of entry into the test system 70 and through the multiple layers of the test system, as aforesaid, before the results are read.

All materials, possibly including any excess marker proteins, that do not become immobilized relative to the protein layer 14 by affixation (e.g., by sticking or binding) to the combinable proteins that are already immobilized thereon may preferably, though not necessarily, traverse through the protein layer 14 to be ultimately captured, trapped and/or absorbed by the absorbent layer 16.

Additional drops of wash buffer may thereafter be required and/or preferentially applied to clear the background of the visible portion 31 of the protein layer 14 so as to provide more unequivocal test result readings.

To recapitulate, and generally speaking, a liquid sample analyte (not shown) may preferably be introduced onto the protein layer 14 through the at least one aperture 24 of the passage layer 12 of the combined testing subassembly 50. Whether under the influence of gravity or some other force, the liquid sample analyte passes through the protein layer 14, and subsequently into the absorbent layer 16.

After the disposable immunodiagnostic test system 70 has been used, it may preferably be allowed to dry, after which it may be disposed of in an ecologically responsible mode of disposal, such as, for example, by incineration.

It is generally thought, though not essential to the basic working of the test system 70, that the denser and more impermeable the passage layer 12, the lower the likelihood of lateral diffusion of added liquid sample analytes.

When the test system 70 is assembled, with the housing aperture 24 substantially aligned "B" with the passage layer 12, the liquid sample analyte is permitted, in use, to traverse through the test system 70.

Though not essential to the invention, it is believed that the upper housing portion 10, the layers 12, 14, 16, and/or the lower housing portion 18 of test system 70 should preferably be assembled in intimate contacting relation with one another, and/or in non-loose fitting relation, so as to provide the test system 70 with improved integrity. It is further believed, though not essential to the invention, that the test system 70 may function effectively so long as the assembled layers are positioned in sufficient intimate contacting relation to cause a liquid sample analyte added to traverse away from its point of entry into the test system 70 and substantially vertically therethrough, under the influence of gravity and/or another similar force.

It is also generally thought, though not essential to the basic working of the test system 70, that the intimate contacting relation of the various layers 10, 12, 14, 16, 18 and the use of interstitial and/or peripheral sealing enables the liquid sample analyte to traverse substantially vertically away from its point of entry, and/or traversing the one or more of layers 12, 14, 16 of the test system 70, with any excess being preferably absorbed by the absorbent layer 16.

The substantially contemporaneous testing of a single liquid sample analyte for the presence of multiple marker proteins, using a single test system 70, may offer significant advantages. These advantages may preferably include a quicker total administration time, and lower cost of materials, when compared to the corresponding administration of four or a like number of separate tests that may otherwise be required on multiple testing systems, along with corresponding controls.

Use of the test system 70 will preferably be simple to use and quick to administer and for provide quick and highly accurate and effective test results, without requiring the purchase of additional specialized equipment nor the supplemental training of already highly qualified testing personnel. As aforesaid, its use preferably also enables a single analyte sample to be tested on a substantially contemporaneous basis for the presence of any of a plurality of causative agents. The test system 70 may preferably be used in a clinical setting, at the point of care, and/or in the field. In fact, the test system 70 preferably may be manufactured and/or assembled in the field and/or in a manufacturing facility that is specifically designed for that purpose, and as such, it preferably also involves lower production and packaging costs. The test system 70 is preferably selectively adaptable to provide qualitative and/or quantitative results, depending on the user's preferences and/or the nature of the test to be conducted.

In addition to all of the foregoing, the test system 70 may preferably be readily disposed of in a simple yet ecologically responsible manner, such as, for example, by incineration over an open fire. As aforesaid, the test system 70 may preferably be selectively adaptable to detect for viral, fungal, bacterial, and/or vector induced infections. Lastly, the test system 70 preferably provides visually discernable test results and/or results within a relatively short period of time.

Of course, other modifications and alterations may be used in design and manufacture of embodiments according to the disposable immunodiagnostice test system 70 without departing from the spirit and scope of the invention. For example, and without limitation, the housing 60 and/or the various layers 12, 14, 16 of the test system 70 may be configured in various geometric shapes, such as, for example, in a square, rectangular, circular, and/or spherical shapes.

Similarly, the test system 70 may be provided with a plurality of test surface areas (not shown) apart from the first and second test surface areas 32, 33 which are described above. In such embodiments, the visible portion 31 of the active surface area 30 might further comprise a plurality of supplemental test surface areas that may, in combination, also be configured in various geometric shapes.

In addition, while an upper surfaces of the passage and protein layers 12, 14 may be shaped so as to define their respective concave portions 56, 58, the passage and protein layers 12, 14 may also each define respective convex, or such other shaped, portions as well.

Furthermore, the labeling indicia 11 may be marked on the upper housing portion 10 or on the passage layer 12 in a manner that is not restricted to being printed, adhered or written thereon.

Moreover, while the above description only describes the presence of one housing aperture 20, multiple respective housing apertures (not shown) may be present for each test system 70.

Furthermore, the units of the disposable immunodiagnostic test system may be arranged in "multiple packs", or in any such other removably connected or frangible relation that may be desired by the end user (i.e., other than in the representative side-by-side removably connected relation format shown in FIGS. 6 and 7).

Similarly, the disposable immunodiagnostic test system 70 may be assembled without an upper housing portion 10, and in such embodiments, it would be comprised of at least the passage layer 12 (possibly with certain labeling indicia 11 marked on its exterior surface), the protein layer 14, the absorbent layer 16, the lower housing portion 18, and the housing side portions 36.

Likewise, only the lower housing portion 18 may be eliminated, such that the disposable immunodiagnostic test system 70 would then be comprised of at least the upper housing portion 10, the passage layer 12 (ensuring that the housing aperture 20 is aligned in substantial vertical registration with the aperture 24 in the passage layer 12), the protein layer 14, the absorbent layer 16, and the housing side portions 36.

Moreover, while the test system 70 may sometimes hereinabove have been described as a rapid assay test in a flow through format, it may instead be constructed in a lateral flow format as well.

The test systems 70 discussed hereinabove are preferably disposable and cost-effective immunodiagnostic test systems that are utilizable for detection of one or more marker proteins in a liquid sample analyte or matrix. As the present invention may be used to test for multiple marker proteins in a single test, as may preferably be administered through the use of a single liquid sample analyte, there is preferably a reduced wait time before the results might be obtainable.

While the present invention is contemplated to be used primarily as an immunodiagnostic system, it may also be manufactured for use in the detection of various marker proteins and such other materials as may be present in tissue culture fluids, plant extracts, seed extracts, soil extracts, and/or water and other aqueous extracts.

As aforesaid, the disposable immunodiagnostic test system 70 according to the present invention may preferably be disposed of in an ecologically responsible and inexpensive manner, such as, for example, by incineration or burning in an open fire.

The disposable immunodiagnostic test system 70 may preferably have lower costs of production and disposal associated with it, in comparison to other analyte testing devices that may be presently available.

We claim:

1. A disposable immunodiagnostic test system for testing for the presence of a plurality of marker proteins in a liquid sample, said test system comprising:
   a passage layer comprised of a first material having a substantially non-porous structure that is configured so as to define at least one aperture therethrough;
   a protein layer comprised of a second material that is configured to enable immobilization of a first and a second combinable protein thereon, the protein layer having a substantially porous structure enabling a portion of said liquid sample to pass therethrough; and
   an absorbent layer comprised of a third material that enables absorption of at least a portion of said liquid sample, the absorbent layer being in intimate contacting relation with the protein layer;
   wherein the at least one aperture of the passage layer is configured to receive the liquid sample; and
   wherein the protein layer comprises an active surface area that is aligned with the at least one aperture of the passage layer so as to be viewable through the at least one aperture, the active surface area comprising a plurality of first test areas arranged in at first ring having a first diameter, and a plurality of second test areas arranged in a second ring having a second diameter, the second diameter being larger than the first diameter, with at least one of the first and second combinable proteins being immobilized in the first test area and at least the other one of the first and second combinable proteins being immobilized in the second test area for binding of said marker proteins with said first and second combinable proteins when the liquid sample comprises such marker proteins.

2. The disposable immunodiagnostic test system of claim 1, wherein the active surface area additionally comprises a control area.

3. The disposable immunodiagnostic test system of claim 2, wherein the control area is disposed at the center of the first ring comprising the plurality of first test areas.

4. The disposable immunodiagnostic test system of claim 1, wherein each of the first material, the second material, and the third material is respectively constructed from one or more different combustible materials, each of the combustible materials respectively being one that produces non-toxic by-products upon incineration.

5. A test system according to claim 1, further comprising a reagent, wherein when at least one of the plurality of marker proteins binds to at least one of the first and second combinable proteins, the reagent is bound to the marker proteins that are immobilized on the active surface.

6. A test system according to claim 5, wherein the reagent comprises a visually tagging substance that provides a colored indicium of the binding of the at least one of the plurality of marker proteins to at least one of the first and second combinable proteins and the immobilization of at least one of the first and second combinable proteins to the protein layer.

7. A test system according to claim 6, wherein said visually tagging substance comprises dyed latex beads.

8. A test system according to claim 6, wherein said visually tagging substance comprises a colloidal gold conjugate substance.

9. A test system according to claim 6, wherein said visually tagging substance comprises a colloidal carbon conjugate substance.

10. A test system according to claim 5, wherein said reagent comprises a protein enzyme conjugate substance, with said test system further comprising an enzyme substrate substance that is operatively bound to said protein enzyme conjugate substance when at least one of the plurality of marker proteins binds to at least one of the first and second combinable proteins.

11. A test system according to claim 10, wherein when at least one of the plurality of marker proteins binds to at least one of the first and second combinable proteins, said enzyme substrate substance displays a colored indicium.

12. A test system according to claim 1, wherein, when at least one of the plurality of marker proteins binds to at least one of the first and second combinable proteins, a portion of said liquid sample passes substantially through said protein layer.

13. A test system according to claim 1, further comprising at least one sealant substantially juxtaposed between said passage layer and said protein layer, and between said protein layer and said absorbent layer.

14. A test system according to claim 1, wherein the portion of the active surface area that is visible through the at least one aperture further comprises a procedural control surface area; and wherein said procedural control surface area is adapted to display a control reading both when at least one of the plurality of marker proteins binds to at least one of the first and second combinable proteins, and when no marker proteins bind to any of the second combinable proteins, so as to operatively confirm that said test system has been used properly.

15. A test system according to claim 14, wherein said procedural control surface area is further adapted to confirm that said test system has been handled and stored properly.

16. A test system according to claim 14, wherein said passage layer is between about 0.2 mm and about 10 mm in thickness.

17. A test system according to claim 16, wherein said passage layer is between about 2 mm and about 4 mm in thickness.

18. A test system according to claim 14, wherein said first material comprises a densely packed paper material.

19. A test system according to claim 18, wherein said paper material is a cardboard material.

20. A test system according to claim 14, wherein said first material comprises a tree bark material.

21. A test system according to claim 14, wherein said first material comprises a packed leaf material.

22. A test system according to claim 14, wherein said protein layer is no greater than about 5 mm in thickness.

23. A test system according to claim 22, wherein said protein layer is between about 0.5 mm and about 2 mm in thickness.

24. A test system according to claim 14, wherein said second material is configured to define pores therethrough, with each of said pores having a pore diameter between about 0.1 microns and about 25 microns.

25. A test system according to claim 24, wherein said pore diameter is between about 0.4 microns and about 2.0 microns.

26. A test system according to claim 14, wherein said second material comprises a nitrocellulose material.

27. A test system according to claim 14, wherein said second material comprises an acetate material.

28. A test system according to claim 14, wherein said second material comprises a nylon material.

29. A test system according to claim 14, wherein said absorbent layer is between about 1 mm and about 50 mm in thickness.

30. A test system according to claim 14, wherein said third material comprises a sponge material.

31. A test system according to claim 30, wherein said sponge material comprises a paper towel material.

32. A test system according to claim 30, wherein said sponge material comprises an acetate material.

33. A test system according to claim 14, further comprising a housing substantially encapsulating said passage layer, said protein layer, and said absorbent layer, with a lower housing portion of said housing being in intimate contacting relation with said absorbent layer and an upper housing portion of said housing being in intimate contacting relation with said passage layer, with said upper housing portion being shaped so as to define at least one housing aperture therethrough, with said housing aperture being substantially aligned in operative fluid communicating relation with said at least one aperture of said passage layer.

34. A test system according to claim 33, wherein said housing is constructed of said at least one combustible material.

35. A test system according to claim 34, wherein said housing is comprised of a housing material having a substantially non-porous housing structure.

36. A test system according to claim 35, wherein each of said upper housing portion and said lower housing portion has said substantially non-porous housing structure.

37. A test system according to claim 33, wherein at least one sealant is substantially juxtaposed between said upper housing portion and said passage layer, and between said lower housing portion and said absorbent layer.

38. A test system according to claim 33, wherein said visible portion of said active surface area is viewable through said housing aperture.

39. A test system according to claim 33, wherein at least one labeling indicium is marked on at least one of an exterior surface portion of said passage layer and an exterior surface portion of said housing.

40. A test system according to claim 39, wherein said labeling indicium is marked on said housing.

41. A test system according to claim 40, wherein said exterior surface portion is provided on said upper housing portion.

42. A test system according to claim 39, wherein said labeling indicium comprises a barcode indicium.

43. A test system according to claim 39, wherein said labeling indicium comprises a text indicium.

44. A test system according to claim 33, wherein said upper housing layer and said lower housing layer are each between about 0.1 mm and about 3 mm in thickness.

45. A test system according to claim 44, wherein said upper housing layer and said lower housing layer are each between about 0.2 mm and about 0.4 mm in thickness.

46. A test system according to claim 1, wherein said combinable proteins comprise proteins adapted to be bound to fungal marker proteins.

47. A test system according to claim 1, wherein said combinable proteins comprise proteins adapted to be bound to viral marker proteins.

48. A test system according to claim 1, wherein said combinable proteins comprise proteins adapted to be bound to bacterial marker proteins.

49. A test system according to claim 1, wherein said combinable proteins comprise proteins adapted to be bound to vector-induced marker proteins.

50. A test system according to claim 1, wherein said combinable proteins comprise proteins adapted to be bound to plant marker proteins.

51. A test system according to claim 14, wherein said visible portion of said active surface area comprises a supplemental first surface area; and wherein in an operative configuration in which at least a portion of the liquid sample passes through the protein layer, said first combinable proteins are immobilized on each of said first test surface area and said supplemental first test surface area.

52. A test system according to claim 51, wherein a higher concentration of said first combinable proteins are immobilized on said supplemental first test surface area relative to a concentration of said combinable proteins on said first test surface area.

53. A test system according to claim 51, wherein said first test surface area and said supplemental first test surface area together notionally define a substantially planar first test ring, with each of said first test surface area and said supplemental first test surface area notionally situated therewithin.

54. A test system according to claim 53, wherein said first test ring substantially circumscribes said procedural control surface area.

55. A test system according to claim 1, wherein said visible portion of said active surface area further comprises a supplemental first test surface area and a supplemental second test surface area; and wherein in an operative configuration in which at least a portion of the liquid sample passes through the protein layer, said first combinable proteins are immobilized on each of said first test surface area and said supplemental first test surface area, and said second combinable proteins are immobilized on each of said second test surface area and said supplemental second test surface area.

56. A test system according to claim 55, wherein said first test surface area and said supplemental first test surface area together notionally define a substantially planar first test ring, with each of said first test surface area and said supplemental first test surface area notionally situated therewithin; wherein said second test surface area and said supplemental second test surface area together notionally define a substantially planar second test ring, with each of said second test surface area and said supplemental second test surface area notionally situated therewithin; and wherein said second test ring substantially circumscribes said first test ring.

57. A test system according to claim 1, wherein said second test surface area comprises a mimicry surface area, wherein said second combinable proteins comprise native proteins biosynthesizable by substantially healthy cells in at least one of said liquid sample and a species furnishing substantially healthy cells; wherein in an operative configuration in which at least a portion of the liquid sample passes through the protein layer, said native proteins are immobilized on said mimicry surface area, such that in said positive result configuration, at least one of said plurality of said marker proteins are bound to said native proteins and immobilized relative to said protein layer.

58. A test system according to claim 33, wherein said passage layer comprises at least two apertures, and wherein an upper surface of said passage layer is configured so as to define a concave portion in which the upper surface of the passage layer has a concave curvature, wherein the concave portion is substantially adjacent to said at least two apertures and substantially aligned with said housing aperture.

59. A test system according to claim 14, wherein an upper surface of said protein layer is configured so as to define a concave portion in which the upper surface of the passage layer has a concave curvature, with said concave portion being substantially adjacent to said visible portion of said active surface area and being substantially aligned with said aperture of said passage layer.

* * * * *